(12) United States Patent
Ninomiya et al.

(10) Patent No.: US 8,593,620 B2
(45) Date of Patent: Nov. 26, 2013

(54) DEVICE FOR MEASURING PROPERTIES OF SCATTERERS, FOR COLOR MEASURING FOR SCATTERED LIGHT OF GEMSTONES, FOR MEASURING BRIGHTNESS OF GEMSTONES, AND FOR MEASURING LUMINESCENCE DISTRIBUTION

(75) Inventors: Hirofumi Ninomiya, Gifu (JP); Akio Kawaguchi, Kawachi-Nagano (JP)

(73) Assignee: Ninomiya Jewelry Co., Ltd., Gifu (JP)

( * ) Notice: Subject to any disclaimer, the term of this patent is extended or adjusted under 35 U.S.C. 154(b) by 99 days.

(21) Appl. No.: 13/104,028

(22) Filed: May 10, 2011

(65) Prior Publication Data

US 2011/0299063 A1    Dec. 8, 2011

(30) Foreign Application Priority Data

May 25, 2010    (JP) .................................. 2010-119349
Nov. 15, 2010   (JP) .................................. 2010-254869

(51) Int. Cl.
*G01N 21/00*    (2006.01)

(52) U.S. Cl.
USPC .......................................................... 356/30

(58) Field of Classification Search
USPC ..................... 356/30–31, 445–446
See application file for complete search history.

(56) References Cited

U.S. PATENT DOCUMENTS

| 2002/0080357 A1* | 6/2002 | Dana .............................. 356/445 |
| 2003/0133121 A1* | 7/2003 | Davis et al. .................... 356/445 |
| 2010/0053627 A1* | 3/2010 | Shyu et al. ..................... 356/446 |

FOREIGN PATENT DOCUMENTS

| JP | 19920083142 A | 3/1992 |
| JP | 19920065658 A | 2/1993 |
| JP | 19930340875 A | 12/1993 |
| JP | 19940011449 A | 1/1994 |
| JP | 19990509630 A | 8/1999 |
| JP | 20060145280 A | 8/2006 |
| JP | 20070508532 A | 4/2007 |

* cited by examiner

*Primary Examiner* — Kara E Geisel
(74) *Attorney, Agent, or Firm* — Trego, Hines & Ladenheim, PLLC

(57) ABSTRACT

A device for measuring properties of scatterers which measures properties of a scatterer from a stereoscopic scattering distribution of the scatterer upon receiving an electromagnetic wave with a certain wavelength distribution is provided. In the device, a scatterer to be measured is placed on a specimen platform; the electromagnetic wave is irradiated onto the scatterer from at least either any one or more directions, or one or more continuous directions of a hypothetical spherical surface having the above-mentioned focal point as its center; scattering waves scattered by the scatterer and reflected off the paraboloidal mirror or projected onto the paraboloidal screen are imaged by the imaging means as planar imaging data; and from thus obtained imaging data, a stereoscopic distribution of the scattering waves generated by the scatterer is obtained so as to measure properties of the scatterer from the distribution result.

3 Claims, 14 Drawing Sheets

$$y = -Ax^2 + \frac{1}{4A} \qquad (A > 0; const.) \qquad (1)$$

$$y = -\frac{1}{2a}x^2 + \frac{a}{2} \qquad (a > 0; const.) \qquad (2)$$

$$y = mx \qquad (3)$$

$$m = \cot\theta = \frac{1}{\tan\theta} \qquad (4)$$

$$\sqrt{m^2 + 1} = \frac{1}{\sin\theta} \qquad (4)$$

$$mp = -\frac{1}{2a}p^2 + \frac{a}{2} \qquad (5)$$

$$\therefore p^2 + 2map - a^2 = 0 \qquad (6)$$

$$p = -ma \pm \sqrt{m^2a^2 + a^2} \\ = a\left(-m \pm \sqrt{m^2 + 1}\right) \qquad (7)$$

$$p = a\left(-\frac{\cos\theta}{\sin\theta} \pm \frac{1}{\sin\theta}\right) \\ = a \cdot \frac{-\cos\theta \pm 1}{\sin\theta} \qquad (8)$$

$$r = a \cdot \frac{1 - \cos\theta}{\sin\theta} \qquad (8)'$$

$$\cos\theta = \frac{a^2 - r^2}{a^2 + r^2} \qquad (9)$$

Fig. 2

$$d\Omega = \sin\theta \cdot d\phi \cdot d\theta \tag{10}$$

$$dS = R^2 \sin\theta \cdot d\theta \cdot d\phi \tag{11}$$

$$dr = a \cdot d\theta \cdot \frac{\sin\theta \cdot \sin\theta - (1-\cos\theta)\cdot \cos\theta}{\sin^2\theta}$$

$$= a \cdot d\theta \cdot \frac{1-\cos\theta}{\sin^2\theta} = a \cdot d\theta \cdot \frac{1}{1+\cos\theta} \tag{12}$$

$$= r \cdot \frac{d\theta}{\sin\theta} \quad (\because \text{Formula.(8)'}) \tag{13}$$

$$dS' = dr \cdot r d\phi$$

$$= \frac{a \cdot d\theta}{1+\cos\theta} \cdot a \frac{1-\cos\theta}{\sin\theta} \cdot d\phi \quad (\because \text{Formula.(8)', (12)}) \tag{14}$$

$$\therefore \frac{dS}{dS'} = \left(\frac{R}{a}\right)^2 \left(\frac{1+\cos\theta}{1-\cos\theta}\right) \cdot \sin^2\theta \quad (\because \text{Formula.(11)})$$

$$= \left(\frac{R}{a}\right)^2 (1+\cos\theta)^2 \tag{15}$$

$$R^2 = (1+m^2)r^2 \quad (\because \text{Formula (4)})$$

$$= (1+m^2)\left(a \cdot \frac{1-\cos\theta}{\sin\theta}\right)^2 \quad (\because \text{Formula.(8)})$$

$$= \left(\frac{1}{\sin\theta}\right)^2 \left(a \cdot \frac{1-\cos\theta}{\sin\theta}\right)^2$$

$$= \left(a \cdot \frac{1-\cos\theta}{\sin^2\theta}\right)^2 = \left(\frac{a}{1+\cos\theta}\right)^2 \tag{16}$$

$$\frac{dS}{dS'} = 1 \tag{17} \qquad d\Omega = dS/R^2 \tag{18}$$

$$= dS \cdot \left(\frac{1+\cos\theta}{a}\right)^2 \tag{19}$$

$$= dS \cdot \left(\frac{2a}{a^2+r^2}\right)^2 \quad (\because \text{Formula.(9)}) \tag{20}$$

Fig. 3

(a)
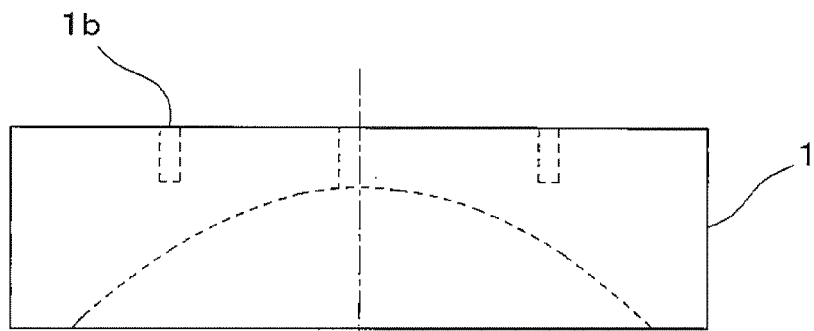
(b)
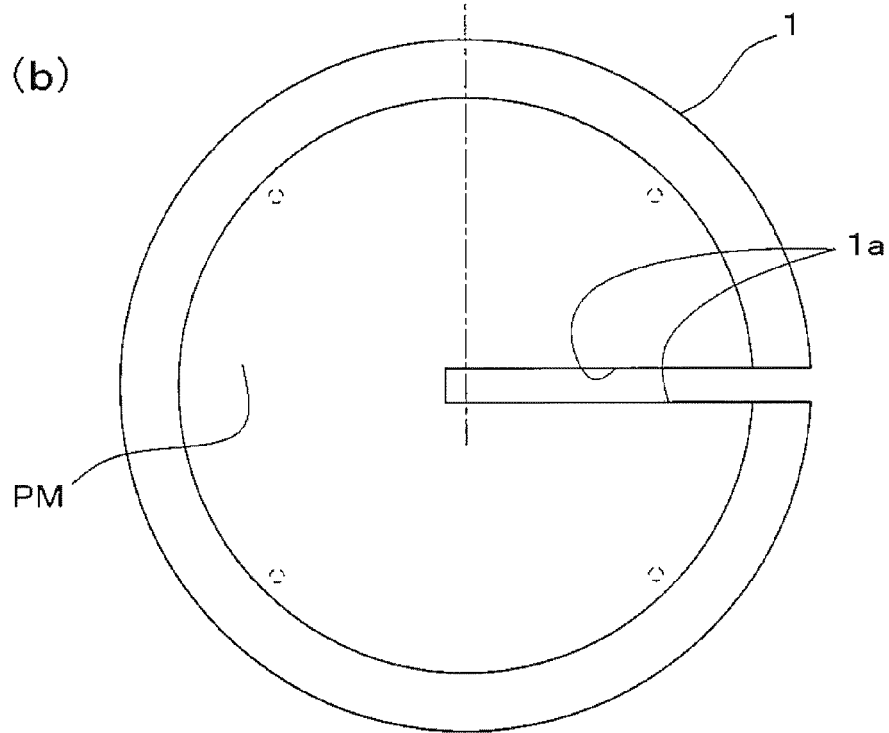
Fig. 5

(a)
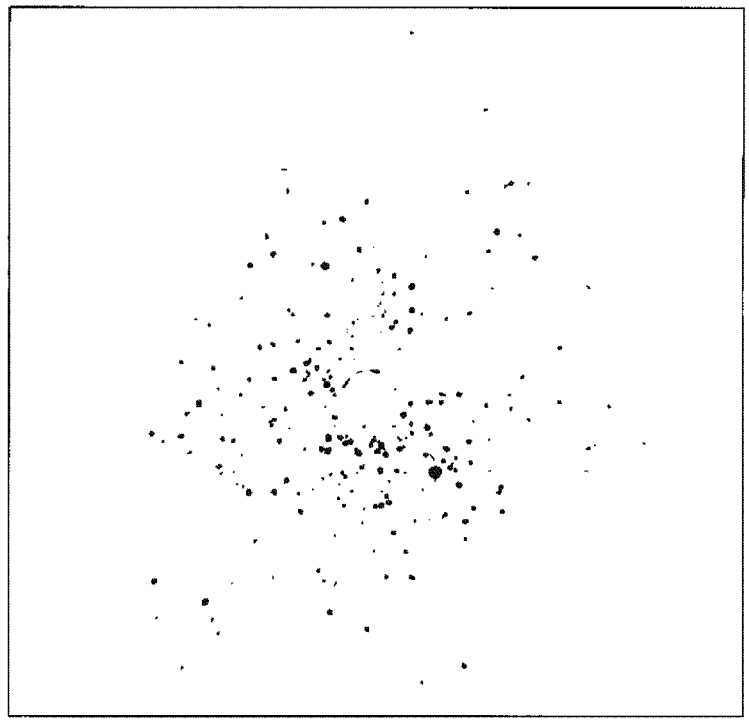
(b)
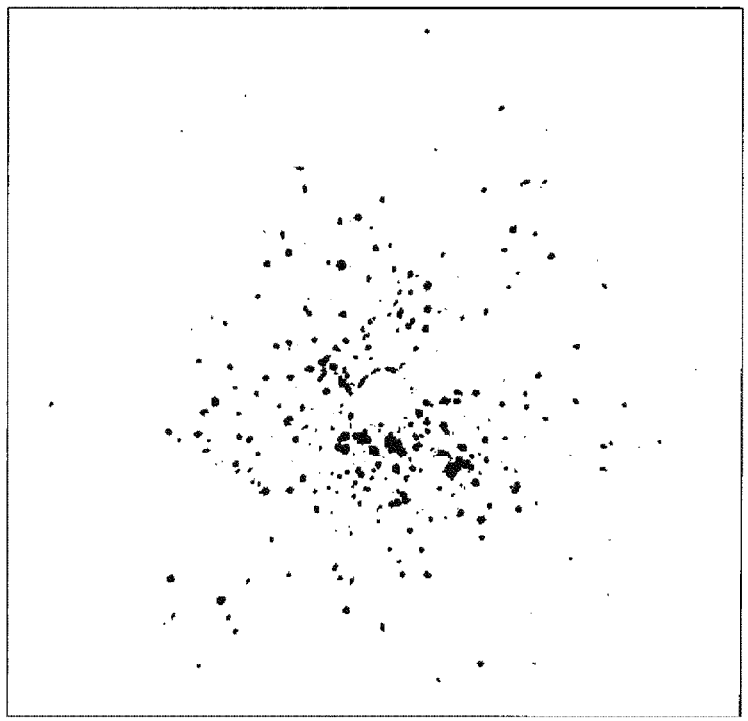
Fig. 6

(a)
(b)
(c)
(d)
all colors
R
G
B
Fig. 13
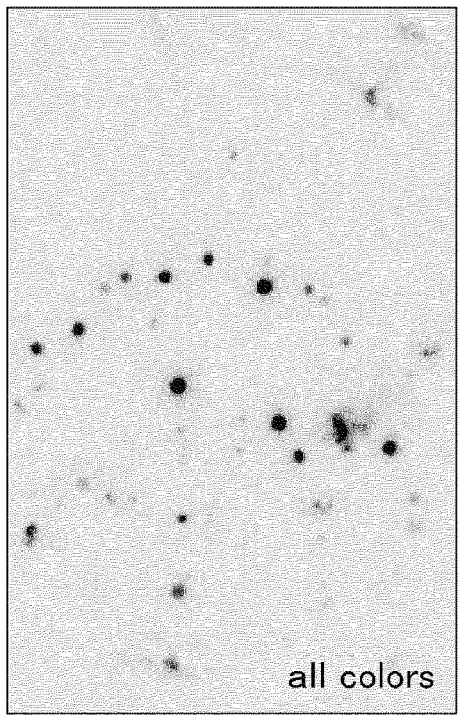
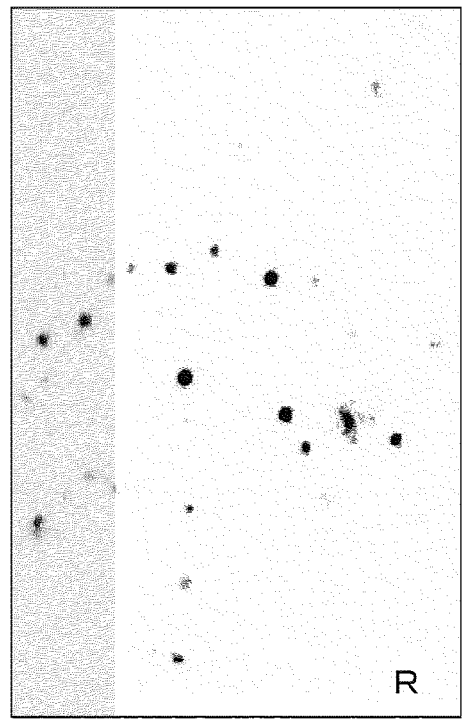
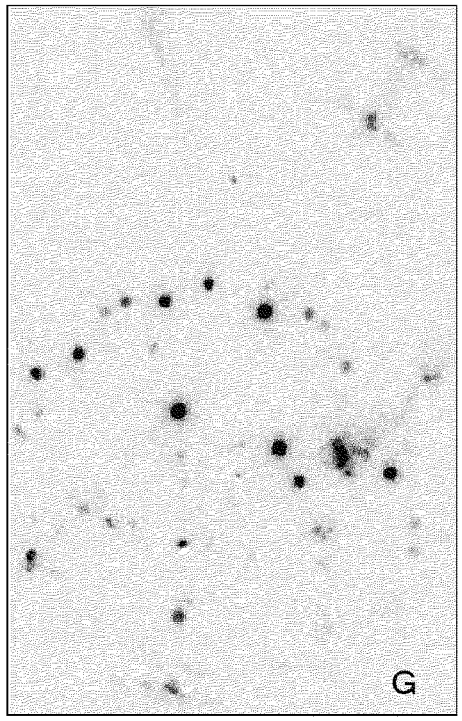
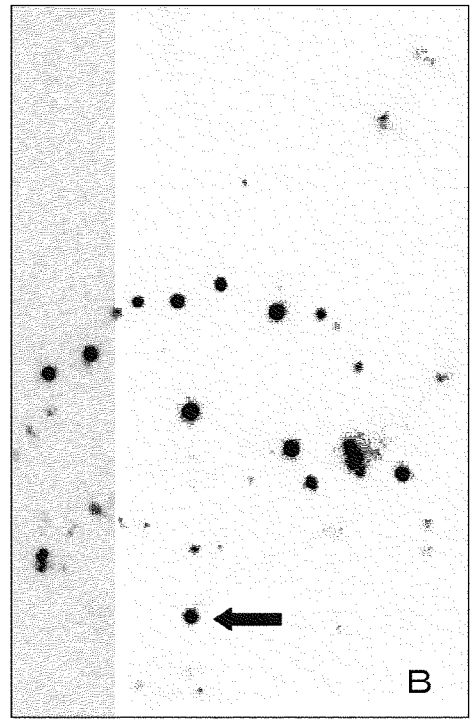

DEVICE FOR MEASURING PROPERTIES OF SCATTERERS, FOR COLOR MEASURING FOR SCATTERED LIGHT OF GEMSTONES, FOR MEASURING BRIGHTNESS OF GEMSTONES, AND FOR MEASURING LUMINESCENCE DISTRIBUTION

RELATED APPLICATIONS

The priority claim under the Paris Convention of the present invention is based on Japanese Patent Application No. 2010-119349 filed on May 25, 2010 (a Device for Measuring Brightness of Gemstones) and Japanese Patent Application No. 2010-254869 filed on Nov. 15, 2010 (a Device for Measuring Properties of Scatterers and a Measuring device for Scattered Light of Gemstones).

TECHNICAL FIELD

The present invention relates to a device which is provided for measuring properties of scatterers from a stereoscopic scattering distribution of the scatterers when they are exposed to an electromagnetic wave with a certain wavelength distribution. The present invention also relates to a color measuring device for scattered light of gemstones, and to a device for measuring brightness of gemstones where the device for measuring properties of scatterers is applied to measurement of the scattered light color of gemstones and to measurement of brightness of gemstones. Further it relates to a device for measuring luminescence distribution of a self-luminescent illuminan.

BACKGROUND ART

The applicant of the present application has proposed a device for measuring brightness of gemstones which measures glitter of gemstones glittering upon receiving natural light in an objective manner in Japanese Patent Application No. 2010-119349 filed on May 25, 2010. The background art of the device for measuring brightness of gemstones will be explained below first by citing the contents of this application which is incorporated herein.

Patent Document 1 discloses an example of the device for measuring brightness of gemstones, which is shown in FIG. 14 of the present application. FIG. 14 is a perspective view of an appearance of the device for measuring brightness of gemstones disclosed in Patent Document 1, which is a background art of the device for measuring brightness of gemstones of the present invention.

This device for measuring brightness of gemstones 60 has diamond as a measuring object. At the center of a transparent glass circular disk 51b, a diamond is placed on the table with its crown being contact with the transparent glass surface, and then covered by a hemispherical dome 51a having a white interior surface. By moving an annular light source 52 up and down right below the glass circular disk 51b, incident light angle from the crown side can be varied. By arranging a detector 55, which is a CCD camera, below the annular light source, only the scattered light essentially vertical with respect to the crown table is measured as bright dot in the field of view.

With this device 60, the crown is set at the bottom, while the pavilion is set at the top. The angle of incident light from the pavilion side is changed with the annular light source 52 moving up and down. Light intensity is measured such that incident intensity for each incident angle (i.e. depending on the change of the height of the annular light source) is detected by the detector 55 arranged immediately below the table surface on the vertical axis, and then accumulated. Scattered light rays in a dispersed manner from the pavilion side are bounced by a white hemispherical dome 51a and reenter. Among them, light rays entering into the detector from the direction of the normal line of the table side is also accumulated as "glitter" into the light intensity value.

Therefore, the device 60 cannot evaluate the size of the bright dots (i.e. solid angles of the scattered light rays), but can only count the number of the intense scattered light rays entering into the field of view. Consequently, small bright dots (scattered light with a small solid angle) are overestimated due to the great number of count, while scattered light with a larger solid angle which comes from larger facets is underestimated.

Since brightness sensible to human eyes depends on the size of bright dots (i.e., size of the reflecting surface, facet), even though the entire amount of scattered light intensity is the same, a diamond "with bright dots each of which has a large reflective solid angle by scattered light and which are small in number" gives greater aesthetic impression. On the contrary, a diamond "with bright dots each of which has a small reflective solid angle by scattered light and which are large in number" is not so attractive as a glitter sensible to human-eyes, which is, however, evaluated as a "specimen releasing great glitter" only due to a large number of count and the total light intensity of the scattered light.

Furthermore, in this device 60, the central axis of the glass circular disk 51b and the axis of the detector 55, i.e., a CCD camera, coincides with each other, and the light source 52 is arranged annularly at a symmetrical position. This arrangement is assumingly selected in order to prevent intense light, i.e., the most intense reflecting light off the table surface, from entering into the detector 55. This arrangement, however, does not necessary reproduce light incidence and scattering under an actual situation of use.

In other words, the measurement method of this device 60, (i.e., a measurement method for counting "scattered light exiting from the direction essentially normal to the table surface" by means of "light incident from the direction other than that normal line to the table surface"), should be regarded as a measurement under a condition different from actual situation of use, also in view of the conditions of light incidence and scattering.

Since both incident light and scattered light (i.e. light recognized to human eyes as "glitter") do not always come from "the direction normal to table surface," under an actual situation of use, for example, the disclosed device model does not simulate an actual situation of use. It is necessary to measure light incidence from any angle direction, and light scattering to any angle direction in order to simulate and quantify an actual case of use.

The above-mentioned problem is partially solved by a device disclosed in Patent Document 2, where a hole is provided at the top of a paraboloidal mirror, and then a measuring object is placed on the focal point of the paraboloidal mirror which is assumingly located near the top. At least two collimated light rays parallel to the central axis of the paraboloidal mirror are irradiated from the paraboloidal mirror side. They are reflected by the paraboloidal mirror, and are irradiated onto the measuring object being located on the focal point. By thus reflected light off the object, bidirectional reflectance distribution function (BRDF) and bidirectional transmittance distribution function (BTDF) can be measured.

Patent Document 2 indeed discloses that light passing through the focal point is parallel to the central axis of the paraboloidal surface of the paraboloidal mirror, and that it also passes through the focal point which reflects the light parallel to the central axis of the paraboloidal surface. But the document does not mention size of the solid angle, the number and the like of light which is necessary for evaluating brightness of a gemstone.

In addition, measurement precision may be affected in some paraboloidal surfaces, depending on their shapes when the relationship between the position of the central axis of the surrounding portions and the reflecting angle is too tight. This possibility is not mentioned in the Patent Document 2, either.

In the above-mentioned Japanese Patent Application No. 2010-119349, a device for measuring brightness of gemstones for solving the above-mentioned object has been proposed. It was found afterwards that this configuration of the device using a paraboloidal surface should not be limitedly used for gemstones but can be applied to a device for measuring properties of scatterers where properties of scatterers are to be measured from a stereoscopic scattering distribution when the scatterers are exposed to electromagnetic waves with a certain wavelength distribution, and also to a color measuring device for scattered light of gemstones where this device for measuring properties of scatterers is used for measuring color of scattered light of the gemstones and further to a device for measuring luminescence distribution of a self-luminescent illuminant.

PRIOR ART DOCUMENTS

Patent Document 1: Pamphlet for International Publication No. 96/23207 (FIG. 4)

Patent Document 2: Japanese Domestic Re-publication of PCT international publication No. 2007-508532 (FIG. 1)

PROBLEM TO BE SOLVED BY THE DISCLOSURE

The present invention was made in order to realize the above-mentioned findings. An object of the present invention is to provide a device for measuring brightness of gemstones in Japanese Patent Application No. 2010-119349. Another object of the present invention is to provide a device for measuring properties of scatterers where, using the principle and the configuration of the device for measuring brightness of gemstones, properties of a scatterer are to be measured from a stereoscopic scattering distribution when the scatterer is exposed to an electromagnetic wave with a certain wavelength distribution, and where irradiating light is not limited to visible light, the measuring object is not limited to gemstones, and the measuring object is not limited to brightness. Still another object of the present invention is to provide a color measuring device for scattered light of gemstones where this device for measuring properties of scatterers is used for measuring color of scattered light of the gemstones and further is used for measuring luminescence distribution of a self-luminescent illuminant.

SOLVING THE PROBLEM

The device for measuring properties of scatterers of the present invention utilizes a principle and a configuration of the device for measuring brightness of gemstones proposed in Japanese Patent Application No. 2010-119349, and was made so that the measuring object is properties of scatterers and light types to be irradiated are varied. It is a device for measuring properties of scatterers which measures properties of a scatterer from a stereoscopic scattering distribution of the scatterer upon receiving an electromagnetic wave with a certain wavelength distribution, including a paraboloidal mirror or a paraboloidal screen; a specimen platform for placing the scatterer on a focal point of the paraboloidal mirror or the paraboloidal screen; a generator for generating the electromagnetic wave; and an imaging means for imaging, as planar images, scattering waves which are scattered by the scatterer upon receiving the electromagnetic wave from the generator, and which are then reflected off the paraboloidal mirror or projected onto the paraboloidal screen, where the scatterer to be measured is placed on the specimen platform; where the electromagnetic wave is irradiated onto the scatterer from at least either any one or more directions, or one or more continuous directions of a hypothetical spherical surface having the above-mentioned focal point as its center; where scattering waves scattered by the scatterer and reflected off the paraboloidal mirror or projected onto the paraboloidal screen are imaged by the imaging means as planar imaging data, and where from thus obtained imaging data, a stereoscopic distribution of the scattering waves generated by the scatterer is obtained so as to measure properties of the scatterer from the distribution result, wherein the scattering waves are obtained in the scope less than $3\pi/4$ (rad.) of a curve on the cross section with center axis of a hypothetical spherical surface with the focal point on it's center. Therefore, scattering waves scattered from a scatterer can be measured from a wide range, i.e., a much larger angular range than that in the case of imaging light on a planar screen, so that images can be obtained from $3\pi/4$ (rad.) of a hypothetical spherical surface. At the same time, measurement can be performed without deteriorating conversion precision, so that properties of the scatterer can be evaluated more precisely.

The paraboloidal surface here means a three-dimensional curved surface made by rotating parabola (curved line on a two-dimensional plane) around its central axis including its focal point.

A color measuring device for scattered light of gemstones of the present invention uses the above-mentioned device for measuring properties of scatterers for the purpose of measuring colors of scattered light of gemstones, where white parallel light is irradiated from the generator; where scattering waves scattered by the scatterer and reflected off the paraboloidal mirror or projected onto the paraboloidal screen are imaged by the imaging means as a planar imaging data, and where from thus obtained imaging data, color scattering or a wavelength distribution of the scattered light of the gemstone can be quantitatively measured.

Regarding the diamond, for example, white color is regarded as best among glittering colors of the diamond. Until now the color has been evaluated by a human-being through visual or sensory inspection by comparing the color of the diamond with a color chart for determining whether it is close to white or not. By means of this device, however, degree of whiteness or RGB ratio can be determined in an objective manner.

A device for measuring brightness of gemstones of the present invention uses the above-mentioned device for measuring properties of scatterers as a device for measuring brightness of gemstones for the purpose of measuring stereoscopic distribution of glitter of gemstones glittering upon receiving natural light, and includes a light source, instead of a generator, for generating parallel light.

With this device for measuring brightness of gemstones having the above-mentioned configuration, a gemstone to be measured is placed on the specimen platform; the parallel light from the light source is irradiated onto the gemstone at least from a direction between a direction of the central axis of the paraboloidal mirror or paraboloidal screen and a direction normal to the central axis, by relatively rotating at least the parallel light and the gemstone each other with at least 90 degrees around the central axis; light then generated from the gemstone is reflected off the paraboloidal mirror or projected onto the paraboloidal screen and is imaged by the imaging means as planar imaging data; and from thus obtained planar imaging data, a stereoscopic luminance distribution of light rays generated by the gemstone, including the size and the number of the light rays, is calculated.

Due to the above-mentioned configuration, the device for measuring brightness of gemstones of the present invention can measure, with a stable precision in an objective manner, the size and the number of light rays from a gemstone glittering upon receiving light similarly as in the case of the actual situation.

It is sufficient to provide a slit at the paraboloidal mirror or the paraboloidal screen or to provide a means to move a light source along an arc within the paraboloidal mirror or the paraboloidal screen in order to irradiate a gemstone with a parallel light from the above-mentioned direction. As parallel light, monochrome laser light, white LED light may be used. Also it is possible to perform observation and measurement using a multiple light sources such that three laser light sources, i.e., red, blue and green laser light sources are switched alternately so as to measure size distribution and the number of bright dots for each color.

A device for measuring luminescence distribution according to the color measuring device for scattered light of gemstones of the present invention, without the light source, measures a stereoscopic luminescence distribution of a self-luminescent illuminant and has the following features. A paraboloidal mirror or a paraboloidal screen is used. When using the paraboloidal mirror, an illuminant is placed on the focal point of the paraboloidal mirror. Next, light emitted from the illuminant on the central axis of the paraboloidal mirror is reflected by the paraboloidal mirror and then imaged by the imaging means. Alternatively, when using the paraboloidal screen, an illuminant is placed on the focal point of the paraboloidal screen. Next, light emitted from the illuminant on the central axis of the paraboloidal screen is projected onto the paraboloidal screen and then imaged. By analyzing either of the imaging data, the stereoscopic luminescence distribution of the illuminant is measured. Thus, this device brings the same advantageous effects of the color measuring device and consequently same advantageous effect of the device for measuring properties of scatterers of the present invention.

BRIEF DESCRIPTION OF DRAWINGS

FIG. 2 shows formulae (1) through (9) used for obtaining the relationship between a solid angle showing a light direction from an illuminant and a distance of the reflected light from the central axis;

FIG. 3 shows formulae (10) through (20) used for conversion with respect to areas of light SB;

FIG. 5(a) is a front view of the mirror body shown in FIG. 4,

FIG. 5(b) is a bottom view thereof;

FIGS. 6(a) and (b) show light emitted from the illuminant and measured by the device for measuring brightness of gemstones;

FIG. 13 shows measurement result by the color measuring device for scattered light of gemstones of the present invention, where (a) shows a scattering distribution of the entire light; (b) shows a scattering distribution of red light (R) thereof only; (c) shows a scattering distribution of green light (G) thereof only; and (d) shows a scattering distribution of blue light (B) thereof only.

EXPLANATIONS OF LETTERS OR NUMERALS

Figure 1:
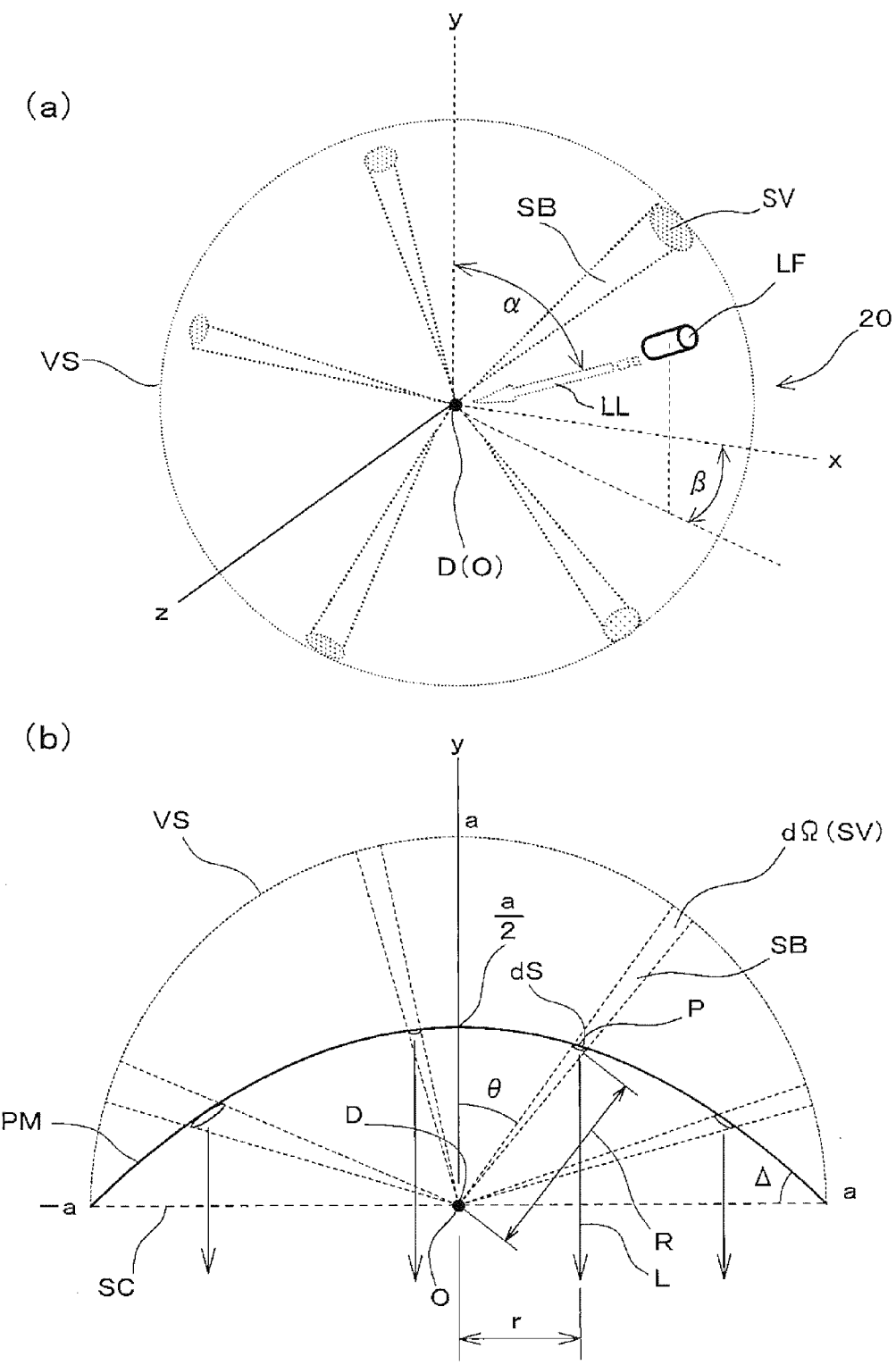
FIG. 1(a) is a conceptual configuration diagram of a device for measuring brightness of gemstones of the present invention.
FIG. 1(b) is a conceptual drawing illustrating a relationship between a paraboloidal surface and a hypothetical spherical surface used in the device.

1—mirror body
1a—slit
2—light source (LF, generator)
3—arc-shaped rail
4—specimen platform
5—support body
6A and 6B—plane mirror
7—CCD camera
8—framework body
20—device for measuring brightness of gemstones
30—device for measuring luminescence distribution
40—device for measuring properties of scatterers
50—color measuring device for scattered light of gemstones
D—illuminant
LL—red laser light
O—focal point
P through P6—light spots on a paraboloidal surface
Q through Q6—light spots on a hypothetical spherical surface
y—central axis
PM—paraboloidal mirror (screen)
SV—light area on a paraboloidal surface (=dΩ)
dS—light area on a hypothetical spherical surface
r—distance from a central axis θ (theta)—solid angle of a direction of illumination (scatterers or reflection wave)

DETAILED DESCRIPTION OF THE DISCLOSURE

The present invention will be explained more in detail below with respect to embodiments with reference to drawings.

<Embodiment 1 of the Present Invention>

FIG. 1(a) is a conceptual configuration diagram of a device for measuring brightness of gemstones of the present invention; (b) is a conceptual drawing illustrating the relationship between a paraboloidal surface and hypothetical spherical surface used in the device. Using these figures, a conceptual configuration of a device for measuring brightness of gemstones will be described below.

As shown in FIG. 1(a), with a device for measuring brightness of gemstones 20 of the present invention, small parallel light rays LL are irradiated from a laser light source LF into a gemstone D (not self-luminescent illuminant, especially diamond) from multiple incident directions. With this arrangement, an actual situation of use of the gemstone (in which light is incident from all directions) is simulated so as to digitalize and quantify "how the illuminant glitters" in the actual condition of use.

"How the illuminant D glitters" can be quantified depending on sizes and areas (solid angle) SV of the light rays SB which are emitted from the illuminant D upon being irradiated with the parallel light LL, and which are then projected onto a hypothetical spherical surface VS (the specimen is placed in the center of the spherical surface). In an actual situation of use of the illuminant D, scattered light is emitted in response to the incident light from all directions toward the specimen. The present measuring device 20, on the other hand, uses only one incident light source LF for the digitalization and quantification, and changes its orientation on a spherical surface (see FIG. 1(a) where polar coordinate angles α and β are changed during scanning) so that "light incidence from all direction" in an actual situation of use can be reproduced.

Then, as shown in FIG. 1(b), a concave mirror PM with a paraboloidal surface is used in order to precisely measure "light (area) dΩ on the hypothetical spherical surface VS." Here, the bright dots S emitted onto the mirror from the specimen (illuminant D) are converted into "size dΩ (area) on the hypothetical spherical surface VS," so that from their statistical distribution, a distribution of the original size of the light dΩ emitted from the illuminant D is analyzed.

<Relationship Between Solid Angle Showing the Light Direction from the Illuminant and the Distance of the Reflected Light from the Central Axis>

As shown in FIG. 1(b), light rays reflected off the paraboloidal concave mirror PM in response to the light SB emitted from the illuminant D (The illuminant is arranged on the focal point of the paraboloidal mirror PM) are all parallel to the central axis (y-axis) of the paraboloidal mirror. There exists a certain relationship between the radius distance "r" from the center of the focal plane and an azimuth (solid angle) θ with respect to light SB. FIG. 2 shows collectively formulae used for explaining the relationship, which will be explained with reference to the formulae below.

The following discussion is based on a premise that there is a light exiting into the direction of (θ, φ) as a three-dimensional polar coordinate. Here, as the "polar coordinate" employs the same concept as latitude and longitude on the globe or celestial sphere surface, the north pole is set to be θ=0°. Then, the "south pole" is considered to have θ=180° (degree)=π (radian), while the "equator" is considered to have θ=90° (degree)=π/2 (radian). The "north hemisphere" can be considered to cover 0≤θ≤π/2 (radian). The specimen (illuminant D) is considered to be at the center of the globe.

Since the system including real and hypothetical projecting and reflecting planes is "axisymmetric," the system is not subject to coordinate conversion in the direction of φ (corresponding to longitude in the globe coordinate). Therefore, only the conversion with respect to θ is considered below.

When y-axis is set as a symmetry axis, and +y axis is set at the convex side of the parabola, an equation of the parabola where its focal point coincides with the origin O, i.e., the spherical center can be expressed as a quadratic formula (1) in FIG. 2.

In general, certain A (A>0) here may be any positive number. Now, light projected and scattered from the spherical center is to be received at a "hypothetical spherical surface" with a radius "a." In order that the "hypothetical spherical surface" coincides with the paraboloid at a position on the horizon (equator), i.e., x-axis or θ=90° of FIG. 1(b), "A" should be selected to be 1/2a. In other words, formula (2) in FIG. 2 can be called to be an equation "for the paraboloidal surface covering the entire celestial sphere having an equatorial radius "a" and having the origin as the focal point" (in embodiments a=100 mm).

Light rays emitted from the origin can be expressed as formula (3) of FIG. 2, which is a linear equation (straight line). The gradient "m" here has a relationship with angle θ against y-axis as expressed in formula (4) of FIG. 2. If a coordinate of an intersection P of formula (2) and formula (3) is set as (p, mp), formula (5) of FIG. 2 and formula (6) of FIG. 2 can be obtained from formula (2). By solving these equations, formula (7) of FIG. 2 can be obtained. Formula (4) can be also expressed as formula (4)' of FIG. 2, so that formula (8) of FIG. 2 can be obtained.

Though not visible in the drawing, from the aspect of a mathematical expression, a linear equation (formula (3)) as straight line connecting O and P expressing the light ray emitted from the origin intersects at two points with a quadratic curve (parabola). Only a value with positive sign (+), however, should be considered as a solution for formula (8), considering the fact that the x coordinate of the intersection P is 0<p<a in the range of 0<θ<π/2.

In fact, if a value with negative sign (−) were included, a single paraboloidal surface could cover the entire sky including the south hemisphere (π/2<θ<π) (except for the south pole) by the principle of the present mechanism. This would be a great advantage, though it would be applied only under a condition that "the paraboloidal surface could be made infinitely deep," which is not realistic in view of the configuration of the mechanism. Realistically, in view of the actual measurement it is more effective to provide another "paraboloidal surface for the south hemisphere."

With the above-mentioned principle, "light exiting at an angle θ with respect to the north pole axis is to be projected onto the paraboloidal surface at a point with x coordinate=a ((1−cos θ)/sin θ." If the paraboloidal surface were a "mirror," the light from the specimen is reflected, so that all light rays with angles θ travel in the direction of −y as parallel light rays with respect to y-axis.

Alternatively, if the paraboloidal surface is a "white screen," light rays emitted from the center point stop there. If these projected images are observed from a sufficiently distant position (i.e., from a position that all images coming into the field of view can be observed as approximately parallel light rays), the light can be seen at the same position as those obtained through the reflection by the "mirror."

This means that, as long as the paraboloidal surface is ideally made by realizing a shape expressed by the equation (2), the images can be observed by using either one of the following optical systems (one which will be described again later with reference to FIG. 9):

(1) an optical system for observing, at infinity (at a position sufficiently distant), light reflected off a mirror having a shape of paraboloidal surface;
(2) an optical system for projecting light reflected off a mirror having a shape of paraboloidal surface onto a planar screen orthogonal to y-axis;
(3) an optical system for observing, at infinity in −y direction, light projected onto a screen having a shape of a paraboloidal surface; and
(4) an optical system for observing light projected onto a semi-transparent screen having a shape of a paraboloidal surface, from +y direction (from the back).

A polar coordinate $(r, \phi)$ on a plane here can be uniquely derived from the original polar coordinate $(\theta, \phi)$ on the spherical surface, by mutually converting formula (8)' of FIG. 2 or formula (9) of FIG. 2. ($\phi$ is not subject to conversion.)

<Conversion of Area of Light Ray SB>

Hereinafter, the conversion of the area of light SB will be described with reference to formula (10) through formula (20) of FIG. 3.

Provided that light scattered, reflected or emitted from a specimen (which is arranged at the center of the globe coinciding with the focal point of the paraboloidal surface) has a solid angle $d\Omega$, the solid angle can be expressed as shown in formula (10) of FIG. 3 using polar coordinate $(\theta, \phi)$ on the spherical surface. In this case, $d\Omega$ is a "rectangular" area with a length $d\theta$ for $\theta$ and a width $d\phi$ for $\phi$. Each bright dot, even with the maximum size, may be considered to have a relatively "minute" area in the space of the entire globe surface or the hemisphere surface.

Now, the following approximation can be considered. For the purpose of discussion, a situation "using a concave mirror with a paraboloidal surface, light emitted from the spherical center is converted into light rays parallel to the axis, which are then projected onto a planar screen SC corresponding to the equator plane" is employed (See FIG. 1(b)). Here, each bright dot can be considered to have a rectangular shape from $(\theta, \phi)$ to $(\theta+d\theta, \phi+d\phi)$.

Then, an area dS of each rectangular shape on the spherical surface at the reflected or projected position (i.e., at a surface of which normal line is directed to the center point, or at a surface receiving the light from the center normally to the surface) is expressed as shown in formula (11) of FIG. 3. As R is a distance between the spherical center and the paraboloidal surface (mirror or screen) as shown in FIG. 1(b), it varies in the range of $(a/2) \leq R \leq a$ depending on $\theta$ $(0 \leq \theta \leq \pi/2$ (rad.))

Provided that the size of each bright dot is sufficiently small, "each of the bright dots having a rectangular shape and projected from the spherical center has again a rectangular shape when projected onto a planar screen as planar light after the light reflected by the paraboloidal mirror." It may be then considered that bright dots projected onto a planar circular screen "are subject to conversion in the radius direction ("r" direction in FIG. 1(b)), while it is not subject to conversion in the angular direction (coinciding with polar coordinate $\phi$ of the spherical surface)."

Furthermore, even if the original scattered light does not have a rectangular shape, since the situation is the same, i.e., "it is subject to conversion in the length $\theta$ direction but not in the length $\phi$ direction," the same argument can be applied as a result with respect to both "the size of the bright dot as a solid angle of the original light projected from the specimen" and "the size of the bright dot reflected from the paraboloidal mirror and projected as a parallel light."

As there is a relationship as shown in formula (8)' and formula (9) of FIG. 2 between the radius position "r" on the planar screen and the angle $\theta$ of the original light SB, formula (12) and formula (13) (because of formula (8)') of FIG. 3 can be derived. Provided that an area of a bright dot after being projected (a fan-shape bright dot projected onto the planar screen after light having been converted into parallel light by a concave-mirror reflection) is dS', formula (14) and formula (15) of FIG. 3 can be obtained.

As R is a distance from the spherical center (focal point of the paraboloidal surface) to the "paraboloidal surface" on which the actual reflection and projection occurs, $R^2=(1+m^2)p^2$ can be obtained, where (p, mp) represents a coordinate of an intersection P of the paraboloidal surface and a straight line having a gradient "m" and passing the center point. Then, the x coordinate p of the intersection P represents a distance from the center to the projected bright dot on a planer screen on which the bright dot is projected (equals to radius "r"). Therefore, formula (16) of FIG. 3 can be obtained.

From these formulae (15) and (16), formula (17) of FIG. 3 can be derived. This means "if the scattered light rays arriving from the specimen arranged on the focal point of the paraboloidal mirror are converted into parallel light rays using a paraboloidal mirror, each of the areas of the bright dots generated after being projected equals to an area of a scattered light ray expected at a reflecting position. (As the reflecting position a hypothetical spherical surface is considered, and an area of light projected on the hypothetical spherical surface is meant here.)"

Besides the areas (of images before and after projection), solid angles $d\Omega$ of bright dots can be discussed and compared in evaluating a specimen. Relationships expressed in formulae (18), (19) and (20) of FIG. 3 can be derived.

In an embodiment, areas of reflected images dS and solid angles $d\Omega$ of bright dots obtained from a concave mirror having a paraboloidal surface with a radius a=100 mm (circle radius of a plane orthogonal to the axis and passing the focal point) are compared and evaluated.

Figure 4:
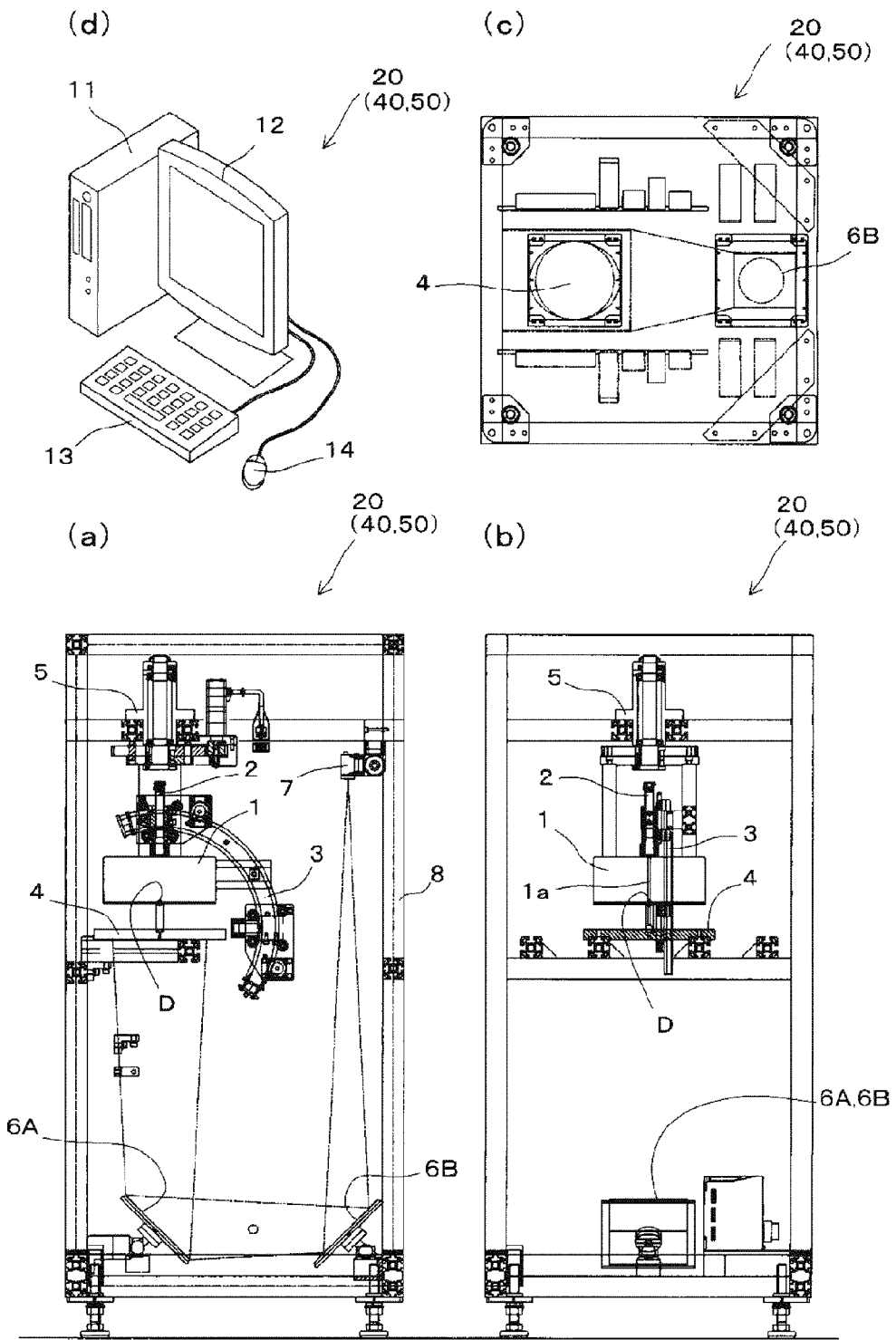
FIG. 4 shows a device for measuring brightness of gemstones which measures brightness of gemstones in accordance with the principle and calculation formulae described with reference to FIGS. 1, 2 and 3, where (a) is a front view of the entire device, (b) is a side view thereof, (c) is a top view thereof, and (d) is a perspective view showing an appearance of a personal computer which performs image processing, calculation and control of the device.

FIG. 4 shows a device for measuring brightness of gemstones which measures brightness of a gemstone based on the principle and calculation formulae described with reference to FIGS. 1 through 3 above; (a) is a front view of the entire device; (b) is a side view thereof; (c) is a top view thereof; and (d) is a perspective view of its appearance showing a personal computer which performs image processing, calculation and control of the device. FIG. 5(a) is a front view of the mirror body shown in FIG. 4, and (b) is a bottom view thereof. Parts which have been already described are given with the same reference numbers and are not explained again below.

The device for measuring brightness of gemstones 20 includes an imaging body 1 which includes in its interior a white-coated paraboloidal screen PM on a paraboloidal surface. The paraboloidal surface has a shape generated by rotating parabola having a given formula around its central axis including its focal point. The device is also provided with a light source 2 (LF) emitting red laser light LL, an arc-shape rail 3 on which the light source is moved following an arc-shape orbit, a transparent specimen platform 4 for carrying an illuminant D, and a support body 5 for integrally supporting the imaging body 1, light source 2 and the arc-shaped rail 3, and for rotating them with respect to the specimen platform 4.

In addition, the device for measuring brightness of gemstones 20 is provided with two plane mirrors 6A and 6B for turning an image projected on the screen PM twice with 90 degrees, a CCD camera 7 for imaging reflected light coming from the plane mirror 6B, and a framework body 8 for supporting these parts.

Furthermore, the device for measuring brightness of gemstones 20 is also provided with a personal computer body 11 for controlling the above-mentioned portions and for processing the obtained data, a flat display panel 12, a keyboard 13 and a mouse 14 in order to control the operation of the device of the present application, and to obtain necessary data by way of data processing.

As shown in FIG. 5, the imaging body 1 generally having a flat cylinder shape includes a paraboloidal screen PM which is arranged in its interior bottom surface. Also, a slit 1a is provided and extended at least from a horizontal plane to a vertical position in order to allow red laser parallel light LL of the light source 2, arranged outside, to irradiate an illuminant D, which is a specimen located within the imaging body 1. A mounting hole 1b for mounting the imaging body 1 to the support body 5 is provided, too.

Since the slit 1a does not reflect the light from the illuminant D (non-reflective part), the entire reflected light from the illuminant D cannot be obtained, which causes a lack of data in this system. By making the width of the light incident narrower depending on the size of the specimen, the lack of data within the observation region can be reduced. In an example, only the area 10 mm (width)×105 mm (length) for a circular area with a radius of 100 mm is this lack area, which does not affect the entire data remarkably.

The light source 2 is driven by an electric driving means having a high controllability such as a servomotor so as to move it smoothly on the arc-shaped rail 3 and keep its angle at any angle position. This arc-shaped rail 3 is fixed outside the imaging body 1 by means of a support body 5.

This type of the device 20 allows to arrange the illuminant D fixed on the specimen platform 4, to move and stop the light source 2 on the arc-shaped rail 3 so as to change the gradient of the parallel light LL from 0 degree to 90 degrees. It is also possible by means of the support body 5 to rotate, with respect to the fixed illuminant D, the light source 2 on a plane having the central line including the focal point of the parabola as a normal line to the plane.

Instead of arranging the slit, a compact light source emitting parallel light and moving on an arc-shaped orbit may be provided inside the paraboloidal screen PM or the paraboloidal mirror in order to irradiate parallel light onto the illuminant D.

FIG. 6(*a*) shows bright dots (light) SB generated such that, using the above-mentioned device, red parallel laser light LL is incident onto the illuminant D (diamond)at a specific angle, the light (scattered red light) is reflected off the paraboloidal screen PM, and the bright dots SB are changed into monochromatic and reversed image. The image to be obtained is observed on the paraboloidal screen PM from the infinity. As the shape of the paraboloidal screen PM is known, a position of each observed bright dot SB on the hypothetical spherical surface LD as well as the solid angle SV as the size of the bright dot can be converted from the distance and the position from the center point.

FIG. 6(*b*) is a "binarized" image of the observed image in FIG. 6(*a*). In other words, in order to measure the size SV of each bright dot SB, size distribution is statistically determined by means of "binarization processing" (which converts a black and white image into a 0 or 1 shape data). Upon this "binarization," statistical distribution of intensity and contrast of the bright dots can be analyzed by adjusting a threshold value.

Figure 7:
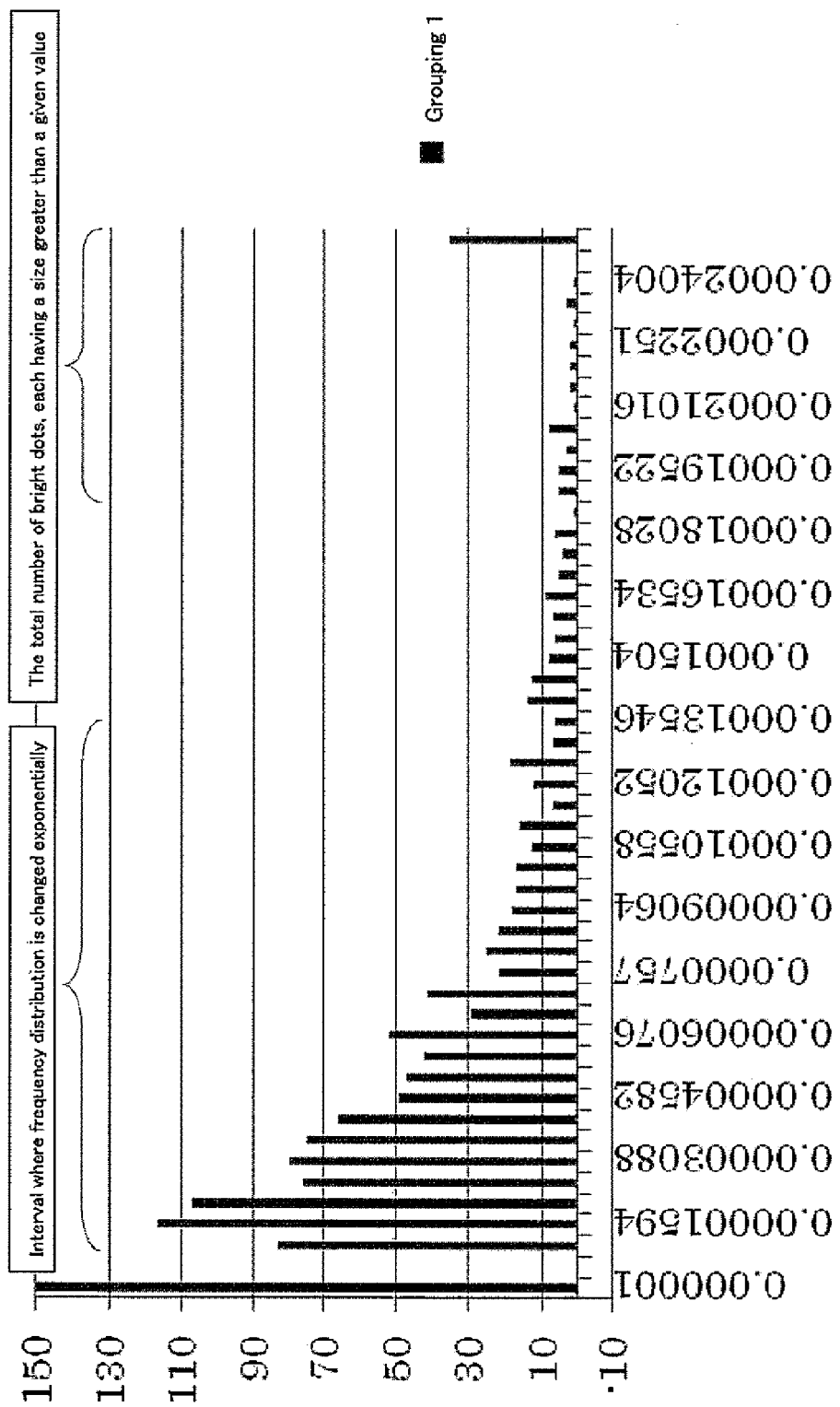
FIG. 7 shows a graph of a frequency distribution (a histogram) of size SV of each of the bright dots SB after the bright dots SB obtained from the image in FIG. 6(b) are converted as a distribution of solid angles on the hypothetical spherical surface LD.

FIG. 7 shows a graph as a frequency distribution (a histogram) of sizes SV of the bright dots SB obtained from the binarized image in FIG. 5(*b*), where the bright dots SB have been converted as a distribution of solid angles on the hypothetical spherical surface LD. Here, as the position of the light source LF is scanned with the polar coordinate (θ, φ) on the hypothetical spherical surface LD being changed, the graph is made from the total distribution of solid angle SV (steradian, strad.)

As a result, the number N of bright dots SB for the solid angle dΩ (strad.) is proportional to an exponential function. In other words, the following empirical rule can be obtained:

$$N(d\Omega) = N0 \exp\{-\lambda d\Omega\}, \text{ where } \lambda > 0, \text{ and } N0 \text{ is a certain} \quad \text{(formula (21))}.$$

The histogram shown in FIG. 7 shows a calculated frequency distribution of dΩ after conversion with respect to all bright dots observed when the polar coordinate (θ, φ) position of the light source LF is changed at ten points, i.e., (0 deg., 0 deg.), (30 deg., 0 deg.), (30 deg., 90 deg.), (60 deg., 0 deg.), (60 deg., 45 deg.), (60 deg., 90 deg.), (90 deg., 0 deg.), (90 deg., 30 deg.), (90 deg., 60 deg.) and (90 deg., 90 deg.)

In this histogram, horizontal axis represents solid angle dΩ, while the vertical axis is the number N(dΩ) of bright dots SB having solid angles dΩ corresponding to a range of each interval.

The ten points can be considered to be incident light directions selected essentially averagely from one-eighth of the entire globe surface. The greater number of selected points as an incident direction and more dense scanning steps can lead to higher measurement accuracy and at the same time to more measurement counts. Irradiation by moving the light source LF in a wider angle range is possible, too.

Numerical values obtained from this frequency distribution data which can be an index for determining "how a scatterer glitters" are considered to be as follows:

(1) attenuation rate λ in an interval where frequency distribution of dΩ is exponential (approximately dΩ=0 through 1.5×10−4 strad.); and (2) the number of bright dots having a size greater than a given value (i.e. having a larger solid angle dΩ, which is dΩ>2× 10−4 strad. or greater, for example).

In addition, attenuation rate λ is changed by changing a threshold value at a "binarization," an image processing procedure. By comparing thus derived statistical average values of the obtained solid angles of the bright dots, (3) an index regarding the contrast can be calculated when bright dots of each scatterer are regarded as intensity. In other words, by analyzing the frequency distribution, indices on the following can be digitalized:

1) whether a specimen in question has many bright dots with a large dΩ or those with a small dΩ, 2) whether the specimen scatters many bright dots having a great absolute value of dΩ, or 3) whether the specimen has a remarkable contrast in bright dots.

<Exponential Function of Frequency Distribution (Histogram) of Sizes>

Among these indexes, a criterion for judging "whether a specimen in question is a specimen having many bright dots with a large dΩ or those with a small dΩ," which is "an attenuation factor λ of the frequency distribution" obtained from the "an exponential region," will be discussed below using the above-mentioned example.

Figure 8:
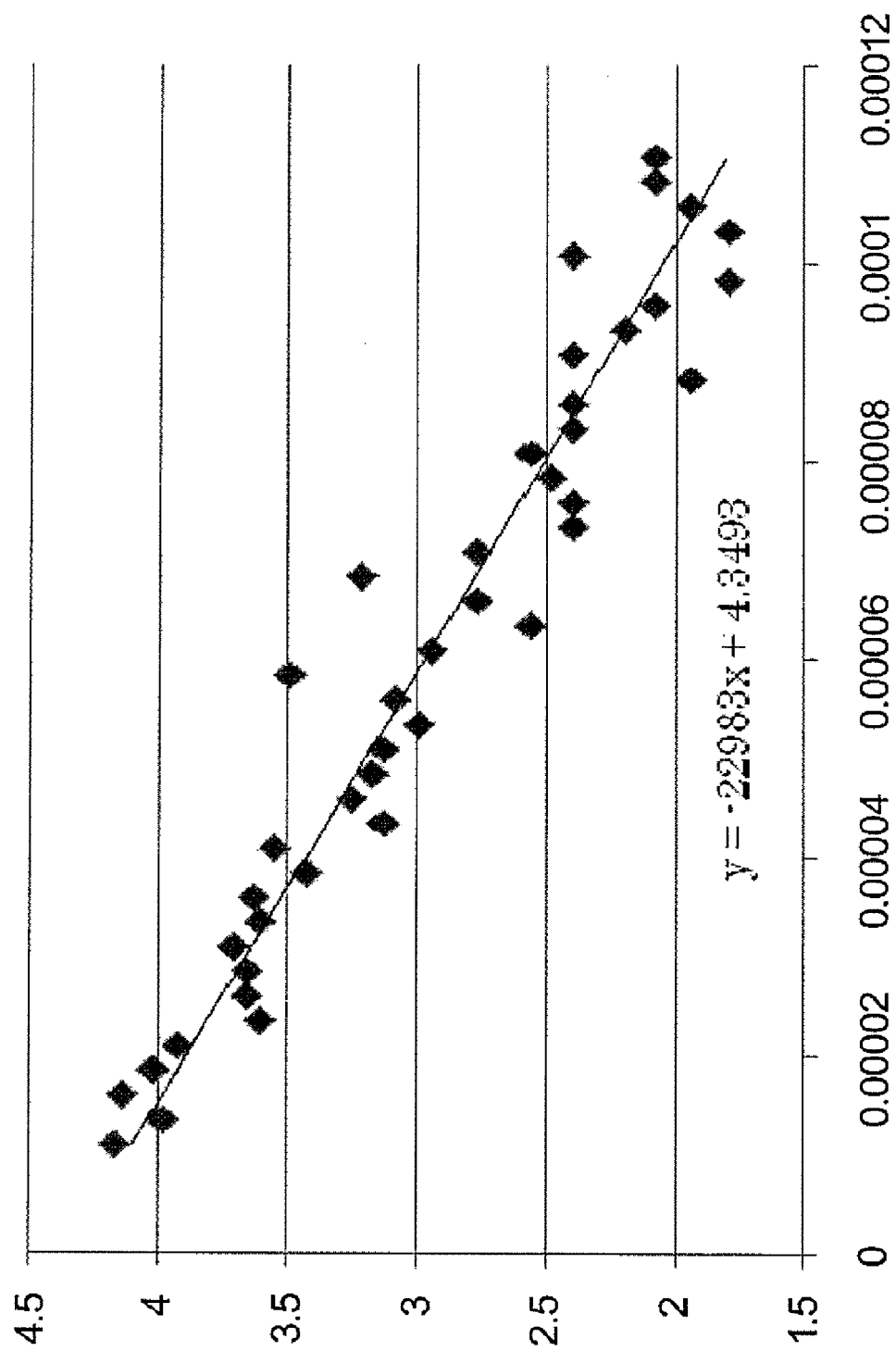
FIG. 8 shows a graph showing an exponential function of the frequency distribution (histogram) of the size.

Provided that number N (dΩ) of bright dots showing an solid angle dΩ has a distribution N(dΩ)=N0 exp{−λdΩ}, logarithms ln{N(dΩ)} of N(dΩ) is taken. When it is plotted with respect to dΩ, a nearly linear relationship as shown in FIG. 8 can be obtained.

Because a gradient value of the straight line corresponds to an attenuation factor with a reversed sign (−λ), the index means as follows:

A specimen with a large λ=Number N(dΩ) of bright dots with solid angle dΩ is attenuated fast=A specimen with relatively small number of bright dots having a large solid angle dΩ, and A specimen with a small λ=Number N(dΩ) of bright dots with solid angle dΩ is attenuated slowly=A specimen with relatively large number of bright dots having a small solid angle dΩ.

As a result, with a device for measuring brightness of gemstones 20 of the present invention, a paraboloidal screen PM is used, a gemstone D to be measured is placed on its focal point. Through a slit 1a provided on the paraboloidal mirror P, laser light LL is irradiated onto the gemstone D at least from a direction between the direction normal to a central axis y of the paraboloidal screen PM and the direction coinciding with the central axis, by relatively rotating the slit 1a and the gemstone D each other with at least 90 degrees. Imaging data of the light generated then by the gemstone D and reflected off the paraboloidal screen PM is analyzed so as to calculate the size and the number of light SB emitted from the gemstone D. Thereby the size and the number of light rays of the glittering gemstone upon receiving light can be measured similarly as in the actual situation, with a stable precision in an objective manner.

The inventors of the present invention believe that a gemstone D emitting a large number of light rays SB with a large size is a sensuously brilliant gemstone glittering well. Therefore, they believe that the device for measuring brightness of gemstones 20 can measure glitter of gemstones, especially diamonds, in an objective manner. They plan to conduct gemstone measurement in the future as much as possible and to clarify the relationship between glitter a human-being senses and measurement values by this device 20.

Instead of the reflective paraboloidal screen PM shown as an example, a paraboloidal mirror can lead to similar effects. In order to irradiate a gemstone with parallel light from the above-mentioned direction, it is sufficient to provide a slit at the paraboloidal mirror or the paraboloidal screen or to provide a means to move a light source along an arc within the paraboloidal mirror or the paraboloidal screen As parallel light, not only monochrome laser light but also white LED light may be used. Also it is possible to perform observation and measurement using a multiple light sources such that three laser light sources, i.e., red, blue and green laser light sources are switched alternately so as to measure size distribution and the number of bright dots for each color.

<Device for Measuring Luminescence Distribution Which is a Base for the Present Invention>

Figure 9:
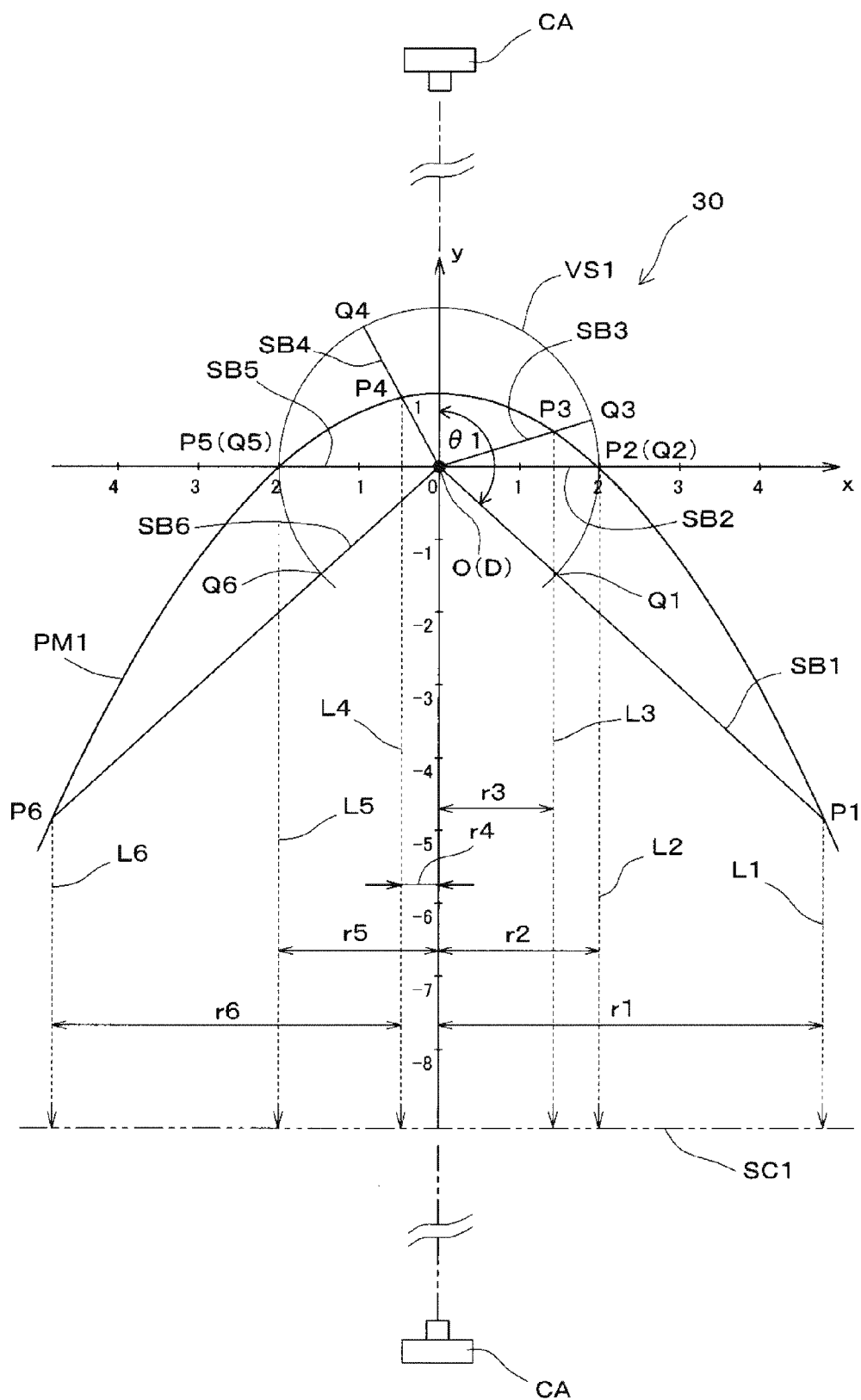
FIG. 9 shows a conceptual drawing showing the relationship between the paraboloidal surface and the hypothetical spherical surface.

FIG. 9 is a conceptual drawing illustrating the relationship between the paraboloidal surface and the hypothetical spherical surface. With reference to FIG. 9, a conceptual configuration of the device for measuring luminescence distribution which is based on the same principle of device for measuring brightness of gemstones of the present invention will be described.

This device for measuring luminescence distribution 30 measures a stereoscopic luminescence distribution of a self-luminescent illuminant D, and has the following features: a paraboloidal mirror PM1 or a paraboloidal screen PM1 is used; in the case of using the paraboloidal mirror PM1, an illuminant D is placed on the focal point O of the paraboloidal mirror; light emitted from the illuminant D on the central axis y of the paraboloidal mirror PM1 is reflected by the paraboloidal mirror PM1, and is then imaged by a CCD camera CA; alternatively, in the case of using the paraboloidal screen PM1, an illuminant D is placed on the focal point O of the paraboloidal screen; light emitted from the illuminant D on the central axis y of the paraboloidal screen PM1 is projected onto the paraboloidal screen PM1, and is then imaged; by analyzing either of the imaging data, the stereoscopic luminescence distribution of the illuminant D is measured.

In the figure, the light rays SB1 through SB6 emitted from the illuminant D are reflected off the paraboloidal mirror PM1, or projected onto the paraboloidal screen PM1. Each of the reflected or projected light spots P1 through P6 is imaged. Each of the projected or reflected light L1 through L6 is parallel to the central axis y. From the position of each light spot r1 through r6, and its size dS1 through dS6, the position θ1 through θ6 and the size dΩ1 through dΩ6 of each light spot Q1 through Q6 on the hypothetical spherical surface VS1 can be calculated from the above-mentioned procedure.

As clearly seen from FIG. 9, and as already discussed, the position θ1 through θ6 and the size dΩ1 through dΩ6 of each of the light spots Q1 through Q6 on the hypothetical spherical surface VS1 can be simply calculated. In addition, due to the relationship between the paraboloidal surface PM1 and hypothetical spherical surface VS1 shown in the figure, a single imaging allows to obtain images of the illuminant D covering the range of 3π/4 (rad.) of the hypothetical spherical surface VS1, which is practical enough. This imaging scope may not be greater than 3π/4 (rad.) or less than 3π/4 (rad.) (This means, that −135 degrees<θ<+135 degrees.)

Figure 10:
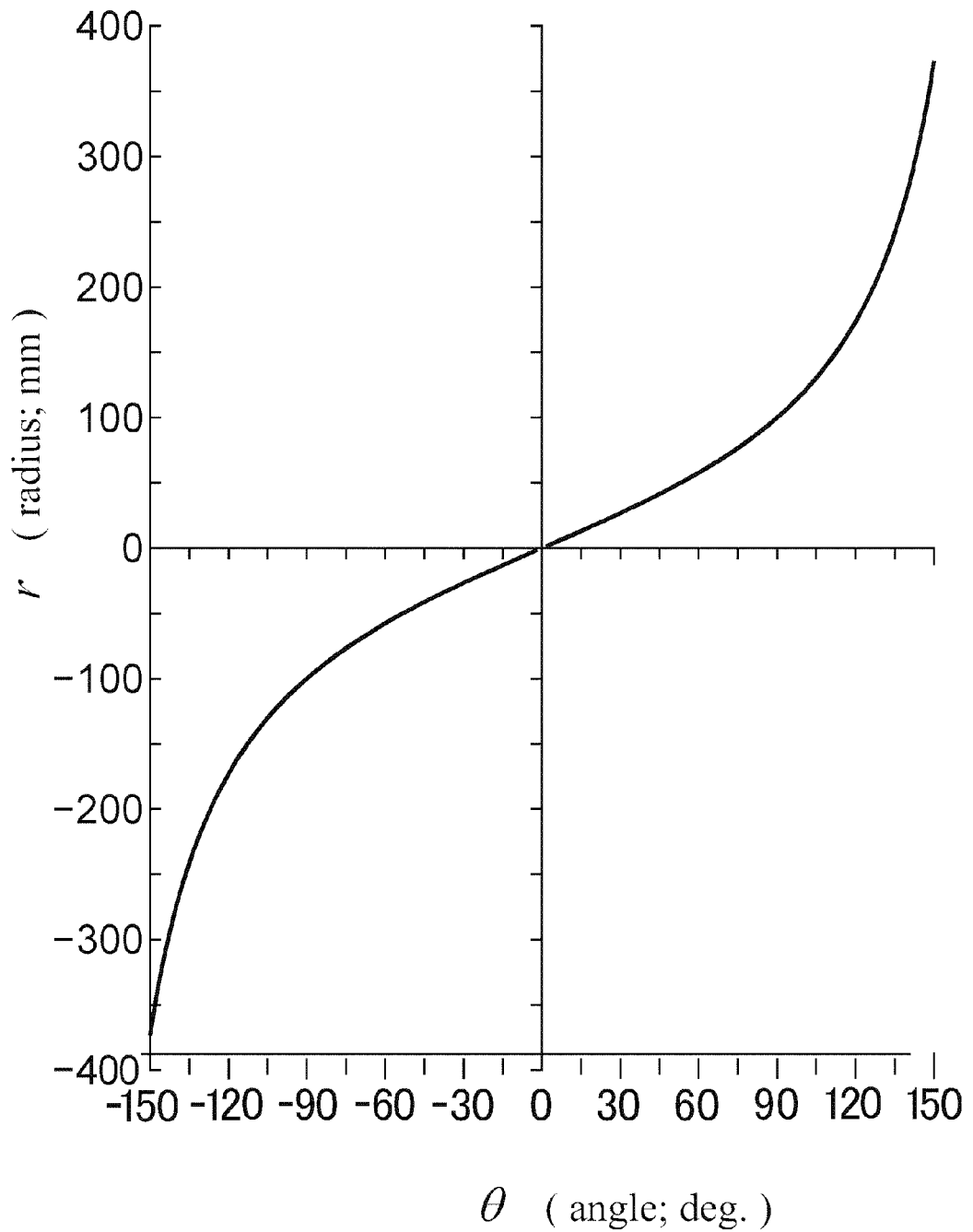
FIG. 10 shows a graph, showing a relation between "r" and "theta" ($\theta$) in FIG. 9.

Furthermore, as can be clearly seen from the relationship between the light spots P1 through P6 on the paraboloidal surface and the light spots Q1 through Q6 on the hypothetical spherical surface, correspondence relationship between P and Q is such that good conversion precision can be obtained with respect to the luminescence for almost all directions, which secures a conversion with a stable precision. FIG. 10 shows a graph, showing a relation between "r (distance from the central axis)" and "θ (solid angle of a direction of illumination)" in FIG. 9. This formula in FIG. 10: r(θ)=a (1−cos θ)/sin θ is equal to the formula 8' in FIG. 2.

In the case of using the paraboloidal mirror, screen SC1 may or may not be used for imaging. The CCD camera CA is preferably located at infinity as an ideal position, but it may be located closer because angular conversion can be performed without difficulty.

In the case of using the paraboloidal screen, on the other hand, the CCD camera CA may be placed either on the convex side or concave side of the paraboloidal screen. This increases degree of freedom in design of the device, and allows the device to be more compact. In addition, the paraboloidal screen may be made of a permeable material such as a synthetic resin, which can reduce a production cost. A camera CA is not limited to a CCD camera, but any imaging means corresponding to an electromagnetic wave in use may be employed.

If light emitted from a specimen is an invisible light such as ultraviolet light or x-ray, fluorescent material may be employed as a material for the paraboloidal screen for luminescence measurement.

By thus utilizing a paraboloidal surface in this device for measuring luminescence distribution 30, luminescence distribution of a self-luminescent illuminant can be measured in a wide angular range in a simple, objective and precise manner.

Accordingly, in the present invention, by using a paraboloidal surface such as a mirror or screen, light emitted from an illuminant (including non-self-luminescent illuminant) can be converted into light parallel to the central axis of the paraboloidal surface. From the data generated by imaging the parallel light by a CCD camera which is a planar light receiving part, light distribution emitted from this illuminant can be stereoscopically measured.

Figure 11:
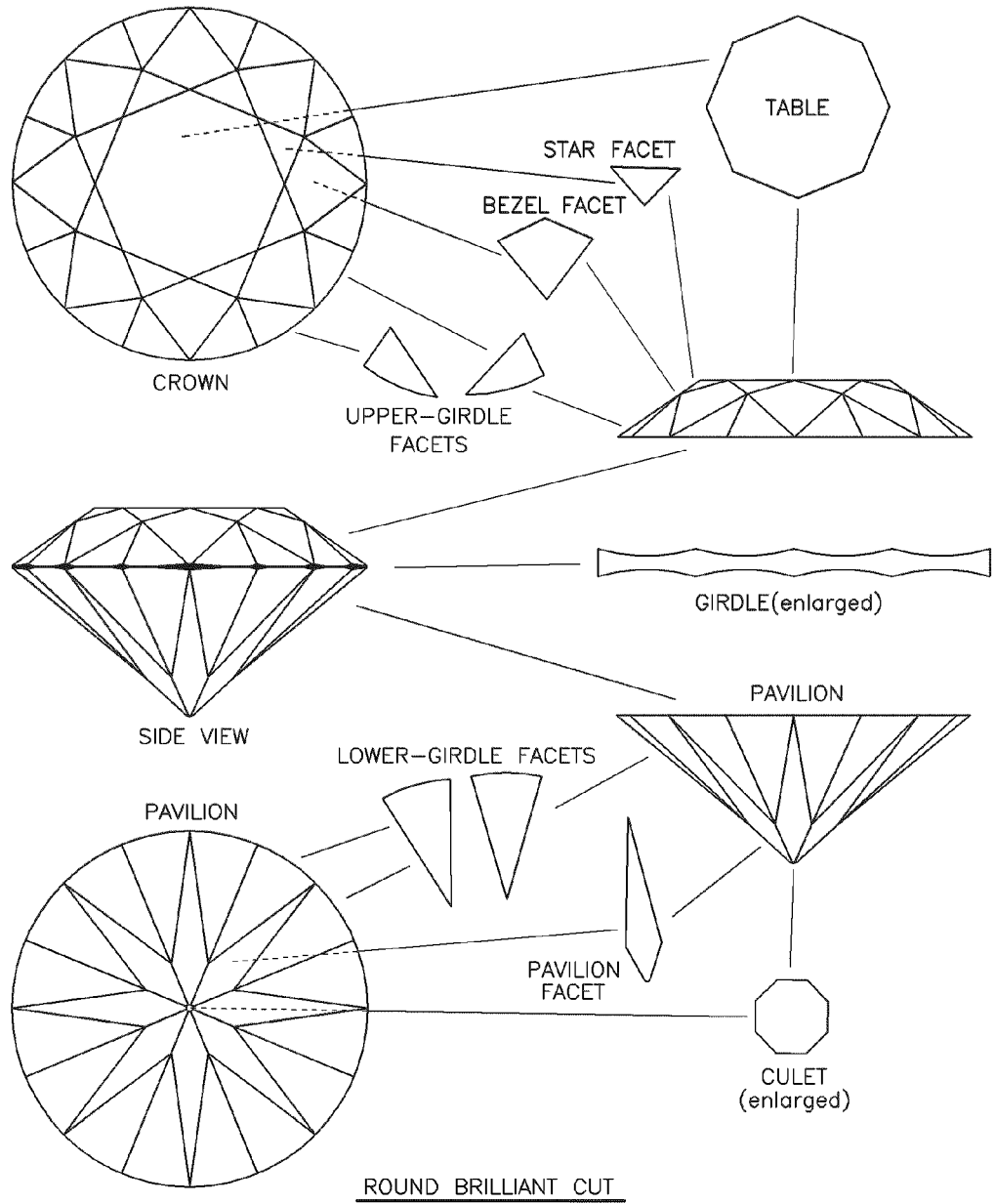
FIG. 11 is a diagram showing a representative cut of a diamond.

FIG. 11 shows a typical cut of a diamond. With reference to this figure, an overview on a diamond, the current status of its brightness measuring, and circumstances how we developed the device for measuring brightness of gemstones of the present invention will be described. This figure is cited from FIG. 6 of ASSIGNMENT 15 in "TEXTBOOK" published by Gemological Institute of America (G.I.A.) in 1972.

A diamond is evaluated by so-called 4C, an evaluation criteria of its value. They include (1) carat (weight), (2) color, (3) cut (proportion, symmetry and polish), and (4) clarity (quality and quantity of the contents).

Among these factors, cut and clarity are related to glitter of the diamond. Clarity is a factor given by nature with which a human-being cannot be involved, while regarding cut, the glitter can be increased or decreased by grinding a surface of the diamond by means of a grinding stone using diamond particles.

At present, as the most typical cut of a diamond, 58-facet cut (including a culet) or 57-facet cut (excluding the culet) is employed, which the applicant of the present application follows, too. FIG. 11 shows a shape and a name of each part of the 58-facet cut.

The shape of the diamond with 58-facet cut roughly consists of a crown which a human-being sees, a pavilion on the opposite side, and a girdle therebetween which is an outer edge portion. The notation "(enlarged)" added to the girdle and the culet portions in the drawing means that these portions are illustrated with an enlarged size.

The crown consists of an octahedron table on the top, eight triangle star facets sloping down from each side of this table, eight nearly rhombic bezel facets sloping down to the girdle and including neighboring sides of two neighboring star facets, respectively, and sixteen upper-girdle facets connecting two bezel facets and a girdle with two straight-line sides and an arc side.

The pavilion consists of eight rhombic pavilion facets consisting of a pair of shorter sides and a pair of longer sides running from the girdle to the culet, sixteen lower girdle facets consisting of two longer sides of neighboring pavilion facets and an arc side achieving the girdle, and a octahedron culet building the lowest side.

Such a 58-facet cut is commonly called as a "round brilliant cut," as shown at the bottom of FIG. 11. For the measurement with the measuring device shown in FIG. 4, the diamond as an illuminant is set on the specimen platform 4 with the culet at the bottom and the table at the top, although the illuminant may be set with a different posture depending on a measurement purpose.

These facets are essentially planar, and have relative angles between one facet and another, which are determined preciously. A diamond cut with the reference angle and flatness is generally called as most beautifully glittering diamond.

The diamond, however, has the highest hardness, so that a grinding stone including diamond particles must be used in order to grind the diamond. If a surface is ground, the grinding stone is worn at the same time as the diamond being ground, so that it is impossible to cut the diamond precisely with target reference angles and flatness.

With a diamond commercially available in a market now usually has an error in angles between the facets at least at two decimal places. Light incident into the diamond having such an error does not generate ideal scattered light (the light is finally emitted as a scattered light after being repeatedly reflected and refracted in a complicated manner within the diamond) because of the above-mentioned error in the angle.

Under these circumstances, as a device for measuring the brightness of diamonds in an objective manner, one example is disclosed in Patent Reference 1, which, however, has the above-mentioned problems. Persons who have gained techniques and experience in the appraisal of gemstones in the Gemological Institute of America currently appraise gemstones as a graduate gemologist. Appraisal by them cannot be regarded as an objective one, because it is anyway an appraisal by human eyes.

There is a proposal to increase the number of cut like 66 facets, 100 facets, 144 facets, 194 facets and 210 facets, for example, to increase the glitter of a diamond. This indeed increases the number of minute glitter, but do not necessary lead to a high-quality glitter as a diamond impressing an observer. Furthermore, the above-mentioned problem of the cut precision may be increased with the increase of the number of facets.

According to a certain patent application, cutting is performed under a special condition being set in the relationship between a facet and another in order to increase glitter of the diamond, but an effect of increasing the glitter cannot be expected from the patent application either, because a precise cutting for fulfilling the condition is anyway impossible due to the above-mentioned cutting precision problem.

Based on a long-time experience as a gemologist, the applicant of the present application knows that a diamond emitting a lot of light rays having a large area is a diamond giving high-quality glitter impressing an observer as a diamond, and, based on the knowledge, has made a device for measuring brightness of gemstones that allows to measure values of such glitter in an objective manner.

The applicant also believes that the principle of this device for measuring brightness of gemstones is also valid for measurement of luminescence distribution of self-luminescent illuminant, so that the applicant has proposed the above-mentioned device for measuring luminescence distribution, too.

A device for measuring luminescence distribution and a device for measuring brightness of gemstones of the present invention are not limited to the above-mentioned embodiments, and various changes and combination thereof are possible within the scope of claims and the embodiments. Thereby these variations and the combinations are included in the right scope the present application.

In addition, since the device for measuring luminescence distribution and the device for measuring brightness of gemstones of the present invention can measure a solid angle of a size and that of a direction for each bright dot, the following is possible, too:

(1) to measure extent of anisotropy ("irregularity") of bright dots. Nearly round bright dots and bright dots with a shape of a comet having a tail can be measured statistically, so that grinding precision and flatness of facets of each specimen can be evaluated;

(2) to measure the extent of position distribution of bright dots within a hypothetical spherical surface (distribution in the orientation ($\theta$, $\phi$) for the incident light from the light source from a specific direction (orientation angle (α, β)). For example, "a specimen prone to emit bright dots in a concentrated manner in the vicinity of the north pole" can be quantitatively distinguished from "a specimen emitting bright dots almost evenly in the north hemisphere." This digitalization can lead to an index for evaluating "a cut causing strong glitter in the direction of table side," for example, and (3) to find in which angular range a specific bright dot can be seen when a light source is dynamically moved. In other words, the movement of each moving bright dot becomes traceable. This could be an evaluation index for accessory articles such as a ring, an earring or a necklace which are often used under a dynamic condition.

Though in the device of the present examples "a specimen is fixedly arranged while a light source being moved in the orientation angle α and β," a relative movement method where "using a paraboloidal convex mirror or screen, a light source is fixed to the north pole position, for example, and a specimen is pivoted in the orientation angle of α and β" (goniometer) may be employed. Alternatively the compromise of the two methods with respect to the position and the orientation of the light source and the specimen may be employed.

<Embodiments of the Present Invention>

The inventors of the present application considers that the device for measuring brightness of gemstones proposed above can be used generally for scatterers, not limiting the measuring object to gemstones. Also, light to be irradiated is not limited to a visible light but includes electromagnetic waves with a certain wavelength distribution. Suppose that scattering distribution property of a scatterer is known. The scatterer is irradiated with the electromagnetic wave, from which a distribution of scattering waves generated from this scatterer is obtained as a planar imaging data. By obtaining the stereoscopic scattering distribution of the scatterer, i.e. the specimen from the imaging data, it can be determined whether both properties are the same. Based on the consideration by the inventors on this kind of use, a device for measuring properties of scatterers of the present invention is proposed.

In this case, the incident light is an electromagnetic wave or a radioactive ray including visible light, infrared light, ultraviolet light (soft or hard), x ray and gamma ray. The electromagnetic wave is such as a monochromatic light with a single wavelength of $10^{-12}$ to $10^{-3}$m or white light having a wavelength distribution.

The scattering wave may be an electromagnetic wave or a radioactive ray with the same wavelength range as the incident wave. The scattering wave may have a different wavelength from that of the incident wave, or may cause difference in the final scattering intensity distribution, depending on the incident wavelength.

Observation Method: Using a paraboloidal surface, through reflection by a mirror or through projection by a screen, intensity and orientation of a scattering wave emitted by a specimen in the three-dimensional space are related to information related in the two-dimensional plane so as to convert into position or intensity information. Then, depending on a material, shape, or reflection- or projection-method of the "paraboloidal surface," the position and intensity information is corrected. This correction is made for considering an evaluation of an effect of a condition of the reflection or projection surface and a deviation of a position of the measured object. Visualization and intensity measurement of both a visible and invisible light may be performed either at the position on the "paraboloidal surface" or after being reflected off the "paraboloidal surface."

In the case of white incident light (incident light bundle having a wavelength distribution), for example, orientation of scattered light varies for each wavelength due to the difference in diffractive index or due to the modulation structure within the specimen(wavelength dispersion). In such a case, filter adjustment of the detector and spectral resolution may be employed so as to perform measurement, by separating the scattering intensity distribution and the like depending on the wavelength and the color of the specimen.

In the case that visible light, or invisible light such as x-ray or a ultraviolet light enters into a specimen, a scattering property (fluorescence) of scattered light from the specimen (the light is emitted with a different wavelength from an incident light wavelength) may be quantified for each orientation in the three-dimensional space so as to observe and measure light.

In the case that invisible light is emitted and scattered from the specimen as a scattered light, the scattered light may be observed and measured by way of luminescence of a fluorescent material coated on the "paraboloidal surface" or by way of intensity accumulation to photostimulable phosphor.

The measuring object is a scatterer including substances which cause reflection or refraction of the incident light (electromagnetic wave) on an optical reflecting or refracting surface (including a crystal optical reflecting surface), or including substances which cause microstructurally-based scattering or diffraction. The scatterer may scatter, diffract or refract an electromagnetic wave which may have a wavelength same as or different from that of the incident light. It may be solid, liquid or gaseous.

In the case of liquid or gaseous scatters, they may be stored in an liquid-tight or air-tight container permeable to the electromagnetic wave in use, respectively, before being placed on the specimen platform 4.

Concrete configuration and its effect of the device for measuring properties of scatterers 40 and the color measuring device for scattered light of gemstones 50 of the present invention are as mentioned in the section of "Means for Solving Problem." The device for measuring properties of scatterers is different from the device for measuring brightness of gemstones shown in FIG. 4 only in that the light source is a generator 2 irradiating not only parallel light, and that the rail 3 rotating the generator 2 up and down is configured such that irradiation by the generator 2 is also possible from just below the specimen platform 4. The color measuring device for scattered light of gemstones, on the other hand, is only different in that the light source 2 irradiates white parallel light.

EXAMPLE 1

Figure 12:
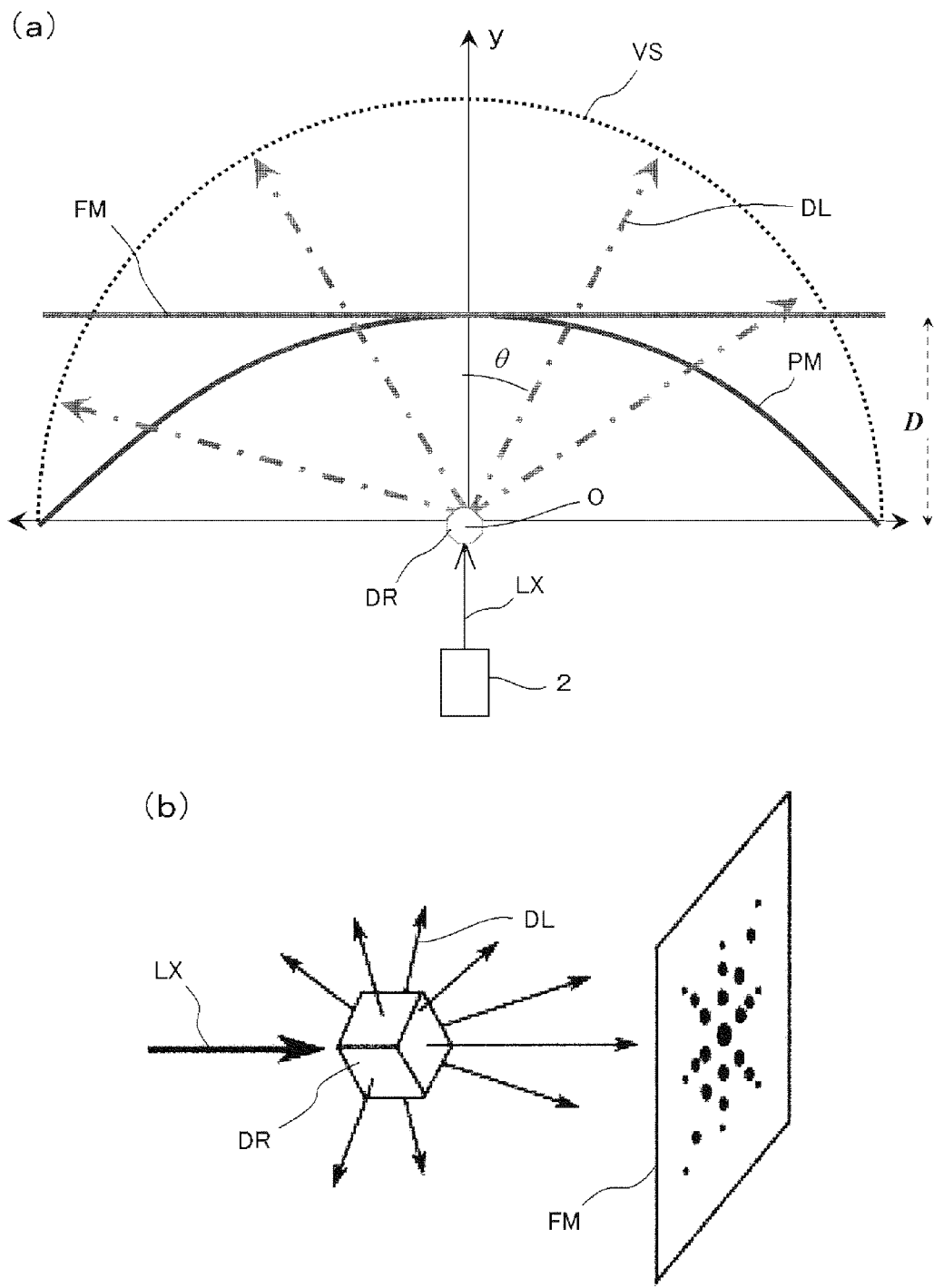
FIG. 12 shows comparison of the feature of the principle of the device for measuring properties of scatterers of the present invention, with that of a measurement device in the background art regarding x-ray diffraction, where (a) shows the feature of the principle of the device for measuring properties of scatterers of the present invention, while (b) shows that of a measurement device in the background art.
Figure 14:
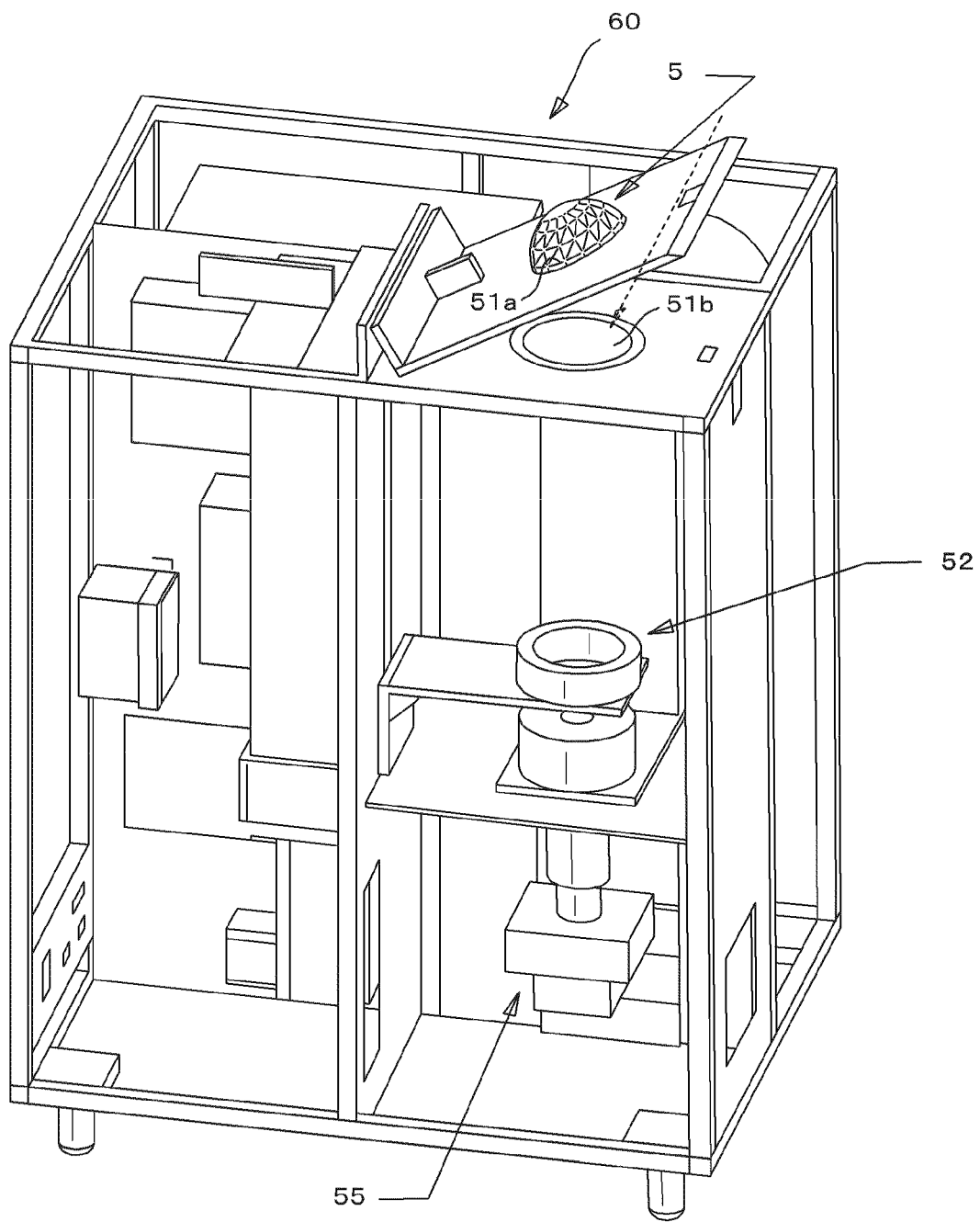
FIG. 14 is a perspective view of the appearance of the device for measuring brightness of gemstones in the background art.

FIGS. 12(*a*) and (*b*) illustrate a difference in operation and effect of the device for measuring properties of scatterers of the present invention being used for the x-ray diffraction, and a general planar screen being used.

In FIG. 12 LX stands for X ray, DR stands for a scatterer, DL stands for scattered light (diffracted light), FM stands for a planar screen, and PM stands for a paraboloidal screen. The paraboloidal screen is a mirror shown in FIG. 5, and is made of transparent acrylic and is coated on its paraboloidal surface with fluorescent material or a coating agent used for an imaging plate (manufactured by GLScan Corporation). O stands for the focal point of the paraboloidal surface.

According to the device for measuring properties of scatterers of the present application, upon receiving scattered light DL from the focal point, the paraboloidal screen PM can receive scattered light in the range of θ=0° through 90°, and also scattered light with θ>90°, i.e., that "below the horizon."

According to the planar screen FM, on the other hand, the light receiving range θ is limited as long as the size R of the device is definite, so that scattered light in the vicinity of the "horizon" (θ is close to 90°) and that in the range of θ>90° cannot be detected.

Though it is possible to shorten distance D between the camera and the planar screen FM (which means moving the screen close to the specimen) so as to widen the range of the detection angle, great difference in the detection performance is caused in the range around θ=0° and that around θ=90°. It is not realistic either to make the size of the device R indefinitely large.

As mentioned above, in the case of the present invention, imaging the scattered light in the angular range greater than the hemisphere is possible, and at the same time, certain precision in the conversion can be obtained, and the conversion formulae are simple. All of these are effects of the present invention.

EXAMPLE 2

Using the device shown in FIG. 4, an experiment was conducted in a manner that white parallel light was generated from the light source (generator) 2, and was irradiated onto a diamond, i.e., a scatter, in a specific angular range. FIG. 13 shows the result obtained from the experiment, which was a scattering distribution (luminance distribution) of the light: (a) shows distribution of the entire light; (b) shows distribution of red light (R); (c) shows distribution of green light (G); and (d) shows the distribution of blue light (B). This color measuring device for scattered light of gemstones employs the same principle and configuration as the above-mentioned device for measuring brightness of gemstones, and is different solely in that white parallel light is irradiated, and that the measuring object is a color tone of the scattered light of gemstones.

From the result of the experiment, distribution of scattered light of the diamond, when white parallel light being irradiated, can be obtained with respect to R, G and B, respectively. By analyzing this distribution result, color tone of the scattered light of a diamond, which is a gemstone, can be measured in an objective manner. Here, it can be seen that there are a lot of blue components as shown in FIG. 13(*d*) by an arrow.

INDUSTRIAL APPLICABILITY

The device for measuring properties of scatterers, the device for measuring brightness of gemstones, and the color measuring device for scattered light of gemstones, and the device for measuring luminescence distribution of the present invention are applicable to an industrial field where, using a paraboloidal mirror or paraboloidal screen, provided that the measuring object is placed on the focal point of the mirror or the screen, scattered light or reflected light from a measuring object is required to be measured with high conversion precision, in a range covering from the zenith (the north pole) of a hypothetical spherical surface having the above-mentioned focal point as its center, to less than 3π/4 (rad.).

The invention claimed is:

1. A method for measuring a stereoscopic luminescence distribution of a self-luminescent illuminant, comprising:
providing a paraboloidal mirror or a paraboloidal screen;
placing said illuminant on a specimen platform which positions said illuminant on a focal point of said paraboloidal mirror or said paraboloidal screen; and
imaging, as planar imaging data, light rays which are emitted from said illuminant, and are then reflected off said paraboloidal mirror or projected onto said paraboloidal screen, and
from thus obtained planar imaging data including the intensity and spectral characteristics of the light rays, as well as the sizes and the number of bright dots when the light rays are represented as discrete bright dots in the imaging data, calculating a stereoscopic luminance distribution of the light rays generated by said illuminant;
wherein for each light ray, an area dS of a bright dot projected on a hypothetical spherical surface is computed based on a measured area dS' of a corresponding bright dot contained in said planar imaging data, wherein said planar imaging data is interpreted as a projected location in 2-D space expressed by the polar coordinates (r, φ), and wherein the bright dot projected on the hypothetical spherical surface represents the size and orientation expressed by the polar coordinates (θ,φ) in 3-D space of the corresponding light ray, to quantify the intensity and the spectral characteristic of each light ray by image transformation and spectral analysis.

2. A device for measuring luminance of a gemstone comprising:
a paraboloidal mirror or a paraboloidal screen;
a specimen platform for positioning said gemstone on a focal point of said paraboloidal mirror or said paraboloidal screen;
a light source configured and positioned to direct parallel light directly at said gemstone when said gemstone is positioned on said specimen platform;
means for rotating said parallel light and said gemstone relative to each other, so as to direct light from said light source onto said gemstone over a range of directions lying between a direction of the central axis of said paraboloidal mirror or paraboloidal screen and a direction normal to the central axis; and
an imaging means for imaging, as planar images which are 2-D information, scattering waves which are generated by said gemstone upon receiving said parallel light directly from said light source and which are then reflected off said paraboloidal mirror or projected onto said paraboloidal screen, and
means for calculating a stereoscopic luminance distribution of light rays generated by said gemstone, including the size and the number of the light rays, from the planar images.

3. A gemstone luminance measuring method comprising:
providing a paraboloidal mirror or a paraboloidal screen;
placing a gemstone to be measured on a specimen platform which positions said gemstone on a focal point of said paraboloidal mirror or said paraboloidal screen;
using a light source to irradiate parallel light directly at said gemstone while said gemstone is positioned on said specimen platform;
wherein the parallel light from said light source is irradiated onto said gemstone over a range of directions lying between a direction of the central axis of said paraboloidal mirror or paraboloidal screen and a direction normal to the central axis, by rotating said parallel light and said gemstone relative to each other, and
wherein light then generated from said gemstone and subsequently reflected off said paraboloidal mirror or projected onto said paraboloidal screen is imaged by said imaging means as planar imaging data which are 2-D information, and wherein from thus obtained planar imaging data which are 2-D information, a stereoscopic luminance distribution of light rays generated by said gemstone, including the size and the number of the light rays, is calculated.

* * * * *